United States Patent
Tai et al.

(10) Patent No.: US 10,512,534 B2
(45) Date of Patent: Dec. 24, 2019

(54) RADIOLUMINESCENT PHOTOTHERAPY EYE DEVICE

(71) Applicant: California Institute of Technology, Pasadena, CA (US)

(72) Inventors: Yu-Chong Tai, Pasadena, CA (US); Colin A Cook, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 15/722,751

(22) Filed: Oct. 2, 2017

(65) Prior Publication Data
US 2018/0092738 A1    Apr. 5, 2018

Related U.S. Application Data

(60) Provisional application No. 62/403,569, filed on Oct. 3, 2016.

(51) Int. Cl.
*A61B 5/06*  (2006.01)
*A61F 2/16*  (2006.01)
(Continued)

(52) U.S. Cl.
CPC .............. *A61F 2/1613* (2013.01); *A61F 2/16* (2013.01); *A61K 9/0051* (2013.01);
(Continued)

(58) Field of Classification Search
CPC .. A61F 2/1613; A61F 2/16; A61F 2002/1699; A61K 9/0051; A61K 49/0015;
(Continued)

(56) References Cited

U.S. PATENT DOCUMENTS

| 5,220,359 A | * | 6/1993 | Roffman | G02C 7/02 |
| | | | | 351/159.03 |
| 6,563,243 B2 | | 5/2003 | Obara et al. | |
| (Continued) | | | | |

FOREIGN PATENT DOCUMENTS

WO    2005079716    9/2005

OTHER PUBLICATIONS

PCT/US2017/054746, "International Search Report and Written Opinion", dated Mar. 27, 2018, 10 pages.
(Continued)

*Primary Examiner* — Aaron F Roane
(74) *Attorney, Agent, or Firm* — Kilpatrick Townsend & Stockton LLP

(57) ABSTRACT

Embodiments of the present disclosure are directed to a phototherapy eye device. In an example, the phototherapy eye device includes a number of radioluminescent light sources and an anchor. Each radioluminescent light source includes an interior chamber coated with phosphor material, such as zinc sulfide, and containing a radioisotope material, such as gaseous tritium. The volume, shape, phosphor material, and radioisotope material are selected for emission of light at a particular wavelength and delivering a particular irradiance on the retina (when implanted in an eyeball). The wavelength is in the range of 400 to 600 nm and the irradiance is substantially $10^9$ to $10^{11}$ photons per second per $cm^2$.

12 Claims, 20 Drawing Sheets

(51) Int. Cl.
| | |
|---|---|
| A61K 9/00 | (2006.01) |
| A61K 51/12 | (2006.01) |
| A61N 5/06 | (2006.01) |
| A61N 5/04 | (2006.01) |
| A61K 49/00 | (2006.01) |
| A61L 27/54 | (2006.01) |
| A61N 5/10 | (2006.01) |

(52) U.S. Cl.
CPC ...... *A61K 49/0015* (2013.01); *A61K 51/1282* (2013.01); *A61L 27/54* (2013.01); *A61N 5/045* (2013.01); *A61N 5/0622* (2013.01); *A61F 2002/1699* (2015.04); *A61L 2300/44* (2013.01); *A61L 2430/16* (2013.01); *A61N 5/0601* (2013.01); *A61N 5/1001* (2013.01); *A61N 2005/0648* (2013.01); *A61N 2005/0656* (2013.01); *A61N 2005/0662* (2013.01)

(58) Field of Classification Search
CPC . A61K 51/1282; A61L 27/54; A61L 2300/44; A61L 2430/16; A61N 5/045; A61N 5/0622; A61N 5/0601; A61N 5/1001; A61N 2005/0648; A61N 2005/0656; A61N 2005/0662
USPC .......................................................... 607/92
See application file for complete search history.

(56) References Cited

U.S. PATENT DOCUMENTS

| | | | |
|---|---|---|---|
| 8,580,163 | B2 | 11/2013 | Biel et al. |
| 8,583,243 | B2 | 11/2013 | Williams et al. |
| 2015/0273179 | A1* | 10/2015 | Krueger ................ A61M 21/02 600/27 |

OTHER PUBLICATIONS

Arden, et al., "Does dark adaptation exacerbate diabetic retinopathy? Evidence and a linking hypothesis", Vision Research, vol. 38, 1998, pp. 1723-1729.

Arden, et al., "A preliminary trial to determine whether prevention of dark adaptation affects the course of early diabetic retinopathy", Eye, vol. 24, 2010, pp. 1149-1155.

Cameron, et al., "Dark adaptation of human rod bipolar cells measured from the b-wave of the scotopic electroetinogram", J Physiol., vol. 5, No. 2, 2006, pp. 507-526.

Okawa, et al., "Atp Consumption by Mammalian Rod Photoreceptors in Darkness and in Light", Curr-Biol., vol. 18, No. 24, Dec. 23, 2008, pp. 1917-1921.

Roos, Magnus W., "Theoretical estimation of retinal oxygenation during retinal artery occlusion", Physiological Measurement, vol. 25, 2004, pp. 1523-1532.

Thomas, et al., "Light adaptation and dark adaptation of human rod photoreceptors measured from the α-wave of the electroretinogram", Journal of Physiology, vol. 518, No. 2, 1999, pp. 479-496.

Yun, et al., "Recent Developments in Laser Treatment of Diabetic Retinopathy", Middle East Afr J Ophthalmol., vol. 22, No. 2, Apr.-Jun. 2015, pp. 157-163.

PCT/US2017/054746, "International Preliminary Report on Patentability," dated Apr. 18, 2019, 9 pages.

* cited by examiner

RADIOLUMINESCENT PHOTOTHERAPY EYE DEVICE

CROSS-REFERENCES TO RELATED APPLICATIONS

This application claims benefit of U.S. Provisional Application No. 62/403,569, filed Oct. 3, 2016, which is hereby incorporated in its entirety for all purposes.

STATEMENT AS TO RIGHTS TO INVENTIONS MADE UNDER FEDERALLY SPONSORED RESEARCH AND DEVELOPMENT

NOT APPLICABLE

BACKGROUND OF THE INVENTION

Many ophthalmological conditions, such as diabetic retinopathy, age related macular degeneration, retinopathy of prematurity, arise from aberrant angiogenesis, driven in part by expression of vascular endothelial growth factor (VEGF) in response to the oxygen deprivation of cells. The oxygen tension within the retina of the eye is of primary concern in these diseases and is a function of supply (oxygen diffusion from the choroid and retinal capillaries) and demand (primarily from photoreceptors and nerve cells). The retina is a multilayered structure composed of various photoreceptor and nerve cells sandwiched between the retinal and choroidal blood supply. Consequently, oxygen delivery to the cells of the retina occurs by oxygen diffusion from either the retinal vasculature or the choroid. This puts an upper limit on the amount of oxygen that can be delivered to the cells within the retina. It has been shown that the metabolic demands of photoreceptors (primarily rods) are inversely proportional to the amount of light they are exposed to. Consequently, metabolic demands are significantly higher in the dark.

The increase in rod metabolism during dark adaptation can lead to hypoxia within the retina as demand outstrips diffusional supply. In patients with compromised retinal circulation, such as diabetics, the elderly, or premature babies, the effect is amplified. This is known as rod driven hypoxia and is becoming understood as a driver for pathogenesis.

Ultimately, treatment of ophthalmological pathologies with hypoxic etiology requires either reversing the oxygen deficiency or interrupting the resulting angiogenic cascade. Several approaches have been developed along these lines. The most clinically significant approach today is the administration of VEGF antagonists into the eye to block the signaling of angiogenesis. This can reduce the ingrowth of new blood vessels onto the retina which helps mitigate vision loss; however, it does not treat the underlying cause of the disease, hypoxia.

Other approaches have looked at enhancing oxygen delivery to the retina by means of implants, which locally increase oxygen tension around the retina to increase diffusional supply. Both passive devices, which shunt atmospheric oxygen from the surface of the eye through to the retina, and active devices, which generate oxygen through electrolysis, have been developed and demonstrated. The clinical efficacy of these approaches is currently awaiting further trials. Neither of these approaches however addresses the fact that dark adaptation drives hypoxia through increased rod metabolism.

It has been proposed that by stimulating the rod cells with low levels of light it may be possible to reduce their metabolic demand for oxygen and thereby reduce or eliminate hypoxia. PolyPhotonix Medical Ltd of Sedgefield, United Kingdom has produced a light emitting sleep mask, known as the Noctura, that utilizes this approach and has demonstrated clinically promising results. The approach however has a number of limitations. Firstly is compliance: sleep masks must be worn to be effective and even during clinical trials routine usage was not achieved. This arises from forgetfulness, inconvenience, and discomfort. Secondly is variability in dosage.

BRIEF SUMMARY OF THE INVENTION

Embodiments of the present disclosure are directed to a phototherapy eye device, which overcomes challenges of compliance and dosage to make ocular phototherapy more effective and appealing. In various embodiments, the eye device includes a number of radioluminescent light sources and an anchor. Each radioluminescent light source includes an interior chamber coated with phosphor material, such as zinc sulfide, and containing a radioisotope material, such as gaseous tritium. The volume, shape, phosphor material, and radioisotope material are selected for emission of light (e.g., peak emission) at a particular wavelength and a particular irradiance. The wavelength is in the range of 400 nm to 600 nm and the irradiance is in the range of $10^9$ to $10^{11}$ photons per second per $cm^2$ (photons/s/$cm^2$). Such emitted light intensity is sufficiently high to induce rod hyperpolarization but low enough to prevent appreciable cone stimulation. In other words, the emitted light helps prevent hypoxia with minimal impact to the eye's sensitivity under photopic conditions.

In an illustrative example, the phototherapy eye device is an implantable phototherapy eye device. This device includes a biocompatible radioluminescent light source implantable inside an eyeball. The biocompatible radioluminescent light source includes one or more walls that form a chamber. A phosphor material coats at least one of the one or more walls. A radioisotope material is within the chamber. An exterior volume of the biocompatible radioluminescent light source is in the range of 1 $mm^3$ to 1000 $mm^3$. The biocompatible radioluminescent light source also includes an anchor coupled with the biocompatible radioluminescent light source. The anchor includes an anchoring surface that is mountable to a surface of an eye tissue.

In a further illustrative example of the implantable phototherapy eye device, the radioisotope material includes gaseous tritium. The radioluminescent light source has a cylindrical shape formed by the one or more walls and having a height and a radius. The height is substantially 0.24 inch (6 mm). The radius is substantially 0.03 inch (0.75 mm). The anchor includes a center body and a plurality of arms extended outwardly from the center body. An end of the cylindrical shape that forms the radioluminescent source is attached to the center body. In this example, the implantable phototherapy eye device also includes a gasket. The gasket receives a portion of the radioluminescent light source and has a partial dome shape in an uncompressed state. A portion of a body of the cylindrical shape extending from its end is disposed in the gasket in the uncompressed state through a hole located substantially at the top of the partial dome shape.

In an illustrative example, the phototherapy eye device is a wearable eye contact lens. This contact lens includes a lens and a radioluminescent light source. The lens has a first chamber and represents an anchor that allows placing the phototherapy eye device on a cornea of an eyeball. The radioluminescent light source includes one or more walls that form a second chamber. The radioluminescent light source is in the first chamber of the lens. Phosphor material coats at least one of the one or more walls. Radioisotope material is within the second chamber.

In a further illustrative example of the wearable eye contact lens, the radioisotope material includes gaseous tritium. The lens includes a plurality of chambers, each containing a radioluminescent light source. In this way, a plurality of radioluminescent light sources are embedded in the lens. Each of the radioluminescent light sources has a cylindrical shape formed by the one or more walls and having a height and a radius. The height is substantially $7.9 \times 10^{-2}$ inch (2 mm). The radius is substantially $6 \times 10^{-3}$ inch (0.15 mm). A total of twenty-four radioluminescent light sources are embedded in the lens according to a pattern. The pattern arranges the plurality of radioluminescent light sources in a longitude-like pattern having an inner circle and an outer circle that are centered around a center of the lens, or alternatively, in an annular pattern with the light sources oriented in a radial direction. An end of each cylindrical shape belongs to the inner circle. An opposite end of each cylindrical shape belongs to the outer circle.

A further understanding of the nature and the advantages of the embodiments disclosed and suggested herein may be realized by reference to the remaining portions of the specification and the attached drawings.

DETAILED DESCRIPTION OF THE INVENTION

Figure 1:
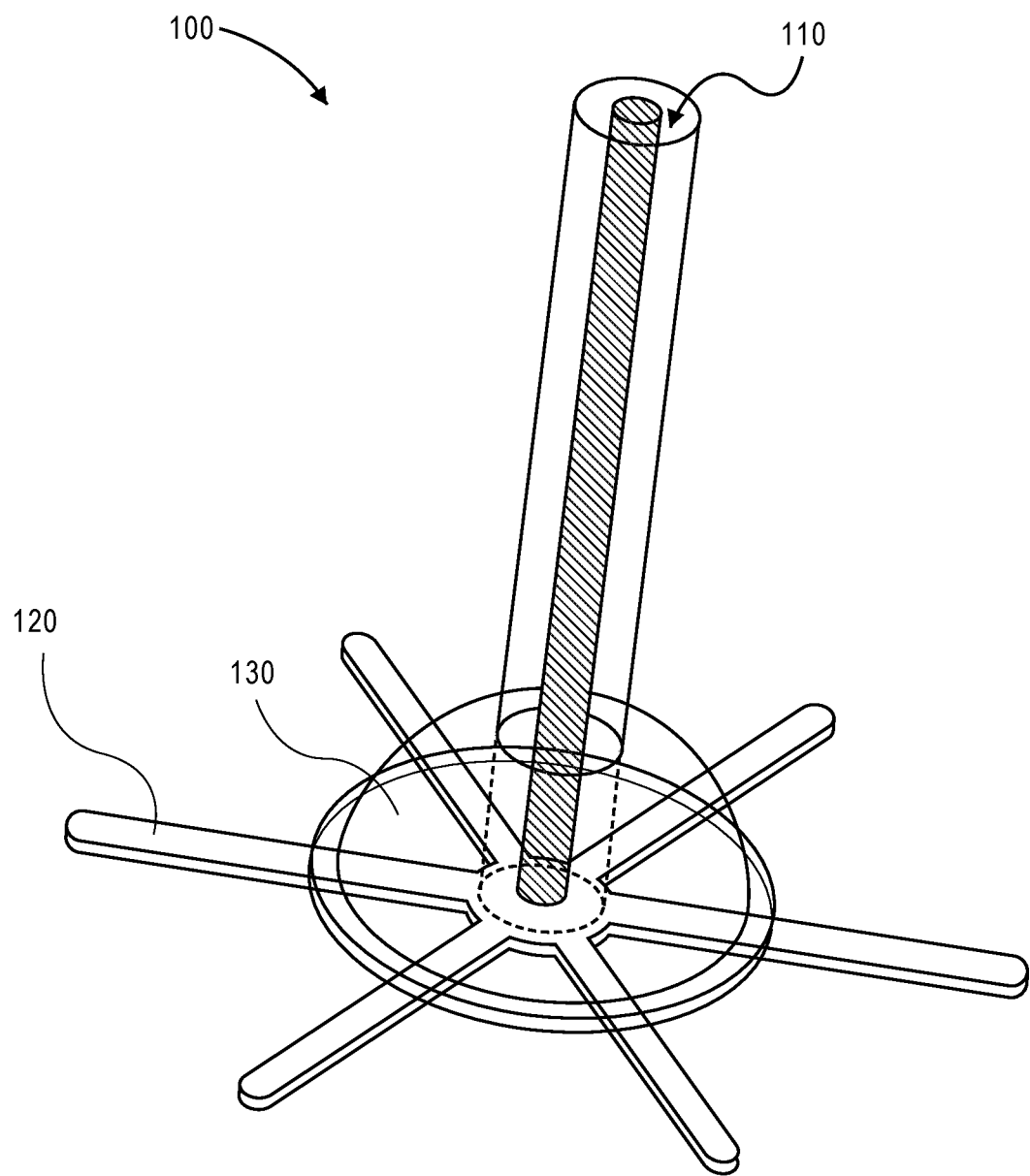
FIG. 1 illustrates an example of an implantable phototherapy eye device, according to embodiments of the present disclosure.

Embodiments of the present disclosure are directed to a phototherapy eye device, which overcomes challenges of compliance and dosage to make ocular phototherapy more effective and appealing. Generally, the phototherapy eye device includes a radioluminescent light source that emits light having, at peak emission, a wavelength between 400 nm and 600 nm ($1.57 \times 10^{-5}$ inch to $2.36 \times 10^{-5}$ inch) and produces an irradiance on the retina of substantially $10^9$ to $10^{11}$ photons/s/cm². The irradiance at the surface of the radioluminescent light source is higher but decreases with the distance away from the source (by conservation of energy) since the surface area over which those photons are spread is increased. Ideally, the wavelength of the light should overlap with the maximum absorbance of rod cells/rhodopsin while being far from the maximal absorbance of blue or green cones, thereby minimizing the visual side effects of continuous phototherapy and maximizing the efficiency of the phototherapy. The irradiance is sufficiently high to induce rod hyperpolarization and low enough to prevent cone stimulation. Hence, where the phototherapy eye device is attached to an eyeball of a subject, the subject's sensitivity to external light is minimally impacted while reducing the rod metabolism and, thus, preventing/mitigating hypoxia. To emit the desired light, an interior surface of the radioluminescent light source is coated with phosphor material, such as zinc sulfide, and an internal chamber of the radioluminescent light source contains a radioisotope material such as a tritium gas. The radioluminescent light source need not rely on other electrical or chemical components to emit the light. Instead, this light source can be dimensioned small enough for implantation inside the eyeball (e.g., in transcleral, intracapsular, intravitreal, or subchoroidal placement) or to be contained in a contact lens, wearable on the subject's cornea (e.g., supercorneal placement). The implantable light source can be a component of an implantable phototherapy eye device, or alternatively, a component of a wearable eye contact lens as further discussed in connection with the figures of the present disclosure.

There are several technical advantages of this phototherapy eye device. Sleep mask approaches rely on transmission of light through the eyelid; however, the degree of transmission depends on a number of factors including eyelid thickness, pigmentation, degree of eyelid closure, and positioning of the mask. Implanted phototherapy eye devices do not necessarily depend on such factors. Further, some do not require a user to remember to put on a sleep mask.

In various embodiments of the present disclosure, the implantable phototherapy eye device provides the long-term treatment and prevention of ocular pathologies arising from hypoxia. Existing devices have utilized electricity or chemical means to produce light. These approaches result in bulky systems that rely on recharging. Unlike these devices, the implantable phototherapy eye device is small, thereby enabling placement in various areas of the eyeball, and utilizes a light source that can provide continuous and near-constant light output through radioluminescence.

Multiple types of radioluminescent light sources are possible, including gaseous tritium light sources (GTLS) (12.32 year half-life) and radium-based light sources (1,600 year half-life). Radioluminescence occurs when ionizing radiation is emitted during radioactive decay and collides with an atom or molecule, exciting an electron to a higher energy state, which subsequently returns to its ground state releasing a photon in the process. A radioluminescent light source can be created by combining a radioisotope and a phosphor material. Gaseous tritium-based light sources have generally a better safety profile over radium-based light sources. GTLS are fabricated by encapsulating tritium gas in a hermetically sealed phosphor coated glass capillary or tube. The use of radioluminescence allows for an incredibly small device suitable for implantation. The implantable phototherapy eye device is produced by attaching a radioluminescent light source (tritium or radium-based) to an anchoring system that holds the radioluminescent light source, when implanted, in the proper orientation within the eye. By virtue of being implanted inside the eye or on the surface of the eye under the eyelid, the photons have a relatively unobstructed path and therefore produce a consistent, predictable dosing of light across patients, irrespective of age, race, gender, or anatomical differences. Additionally, the implanted radioluminescent light source provides continuous phototherapy to the patient thereby mitigating dark adaptation induced hypoxia. This protects the patient during low light situations beyond sleeping (e.g. nighttime activities, caving, diving, theatres).

In an example, GTLS can be made in incredibly small packages and still provide sufficient light output to prevent dark adaptation. To minimize the visual side-effects of the continuous phototherapy, a wavelength is selected based on phosphor material coating inside the GTLS. The wavelength is close to the maximum absorbance of rod cells (500 nm), but sufficiently far from the maximal absorbance of the blue (425 nm) or green cones (535 nm). The light intensity is also sufficiently high to induce rod hyperpolarization but low enough to prevent cone stimulation, which starts around $10^{12}$ photons/s/$cm^2$ on the retina. An irradiance on the retina of around $10^9$ to $10^{11}$ photons/s/$cm^2$ is suitable and achievable by radioluminescent light sources. The irradiance as a function of position on retina can also be tuned and this is useful since rods are more abundant peripheral to the macula, where cones dominate. This spatially variable irradiance can be achieved through light source shape, position, filtering, or reflector design, or lensing.

Additionally, light emitted from the GLTS and hitting the retina is diffused and, thus, does not form a noticeable image. The implantation of the GTLS also takes advantage of the Troxler effect, whereby static images or irradiance on the retina becomes gradually subtracted from conscious vision. Since the implant can be anchored to the eye, the GLTS moves as the eye moves and, thus, there is minimal temporal change to the spatial irradiance. As such, the subject typically does not notice the emitted light after implantation. This is in contrast to the existing devices that rely on light passing through the eyelids. Since the eyeball moves independent of the external light source, temporal variations in spatial irradiance occur and are picked up by the conscious vision creating unpleasant distraction for the subject utilizing the current devices.

Generally, the radioluminescent light sources are ideally suited for ocular implants due to their small size, reliability, safety, and lifetime. These features support the implantable nature of a phototherapy eye device, the ability to anchor the device to the eye, and the ability to provide continuous and consistent dosage, irrespective of the subject.

Nonetheless, other light sources exist and can be adapted for implantable phototherapy devices. These include light emitting diodes, electroluminescent sources, chemiluminescent sources, electrochemiluminescent sources, bioluminescent sources, phosphorescent sources, fluorescent sources, and upconverting crystals. Upconverting crystals can be implanted in the eye or blended in a contact lens and then a longer wavelength light is applied from outside the eye to stimulate emission of the shorter, therapeutic wavelength. This approach can benefit from the near-infrared window in most biological tissues to penetrate the eyelid. Since it utilizes infrared, the light does not visually affect individuals without upconverting crystals.

There may also be a desire to allow the device to be turned on, off, or attenuated. This can be accomplished by incorporating an activatable shutter or dimmer into the light source. Such systems can utilize suspended particles, microblinds, polymer dispersed liquid crystal, electrochromics, thermochromics, and/or photochromics to achieve this dynamic control of light levels. For example, magnetic nanoparticles can be dispersed in a thin encapsulated layer of liquid around the light source and can be concentrated using an external magnet to attenuate light. In another example, an attenuating coating on the light source can be applied which degrades with a time constant similar to the half-life of the radioluminescent source so that a more constant light output from the device can be achieved.

In an example, the implantable phototherapy eye device includes an anchoring system and a radioluminescent light source, such as a GTLS manufactured by Trigalight of Niederwangen, Switzerland. The GTLS is cylindrically shaped with a 1.5 mm (0.06 inch) diameter and a 6 mm (0.24 inch) height. The GTLS was tested for light output by holding it in a vertical or horizontal orientation and moving it by given distances away from a power meter, model 1936-R from Newport Corporation of Irvine, Calif., with photosensor wand, model 918D-ST-UV from Newport Corporation. The GTLS was shown to produce sufficient irradiance at up to 25 mm (0.98 inch) for suppression of the rod dark current in both horizontal and vertical orientation. Additionally, the GTLS were placed in an eye model with light sampling ports to measure the spatial distribution of light expected in an actual eye. With the GTLS placed at 22.5 mm (0.88 inch) from the retina in the eye model, the retinal irradiance was measured to vary between 9.96E+9 photons/s/cm$^2$ at 15 mm (0.59 inch) from the retina and 2.82E+09 photons/s/cm$^2$ at 1.2 mm (0.047 inch) from the retina.

The shape of the light source plays an important role in the spatial distribution of light intensity received by the retina. Cylindrical light sources produce higher intensities parallel to their length and lower intensities perpendicular to their length. Disk or flat shaped light sources provide greater light intensity perpendicular to their faces compared to their sides. The selection of light source geometry can therefore be relevant. Additionally, the geometry of the light source affects its ability to be implanted in the eye (e.g. incision size). Cylindrical GTLS allow implantation with a small incision relative to other geometries producing comparable light output. Light sources can also be covered with a photomask to produce customized spatial patterns of irradiance on the retina.

The anchoring system of the implantable phototherapy eye device maintains the light source in the proper orientation within the eye. In an example, the anchoring system is usable for transcleral anchorage and includes a skirt having a hemispherical shape and anchoring arms/plate. When inserted the scleral tissue sits between the skirt and the anchoring arms/plate, causing compression of the skirt thereby forming a tight seal against the inner face of the sclera preventing leakage from inside the eyeball to the outside of the sclera. The effectiveness of this anchoring system was demonstrated by comparing the permeation of water through an enucleated porcine eyeball implanted with a device compared to permeation without a device. There was no significant difference in permeation, implying a robust seal. The anchoring arms/plate sit on the outer surface of the sclera, under the conjunctiva and prevent the device from falling into the eye.

The arms provide grip points during insertion for the surgeon and are sufficiently long so that the entirety of the skirt can pass through the incision and into the eye without the arms also entering. This facilitates simple and dependable implantation. The arms can be shortened following implantation of the implantable phototherapy eye device.

The anchoring system can be made of medical grade polydimethylsiloxane (PDMS) material, known for its favorable biocompatibility profile, durability, and optical clarity. The skirt can be formed in a hemispherical shape by conformal coating of PDMS onto a hemispherical mold and curing (e.g. by means of spray coating or spin coating). The hemispherical geometry of the skirt allows it to form a seal against the inside face of the sclera by acting as a spring to provide compression. The arms/plate can also be made of PDMS and fabricated using dry film photoresist molds. The skirt was centrally punched to allow it to slide onto the cylindrical GTLS where it was secured by gluing with PDMS. The arms/plate were similarly fixed to the GTLS end with PDMS. The entire device can optionally be coated with Parylene to improve biocompatibility and mechanical properties.

Alternative systems for anchoring radioluminescent light sources are possible depending on the position on or within the eye that is chosen. The compact nature of the implantable phototherapy eye device enables implantation in many manners: transcleral, intravitreal, within the aqueous humor, within the lens capsule, or subchoroidal. Transcleral anchorage has been demonstrated in enucleated porcine eye models. By maintaining the light sources off the optical axis of the eye, central vision can be maintained while still stimulating the retina with sufficient light from the radioluminescent light source. For implantation into the aqueous humor or vitreous humor, anchorage of the device can be made into the sclera or cornea by means of a suture or anchor.

Hence, the implantable phototherapy eye device enables utilizing radioluminescent light sources to provide continuous ocular phototherapy. The compactness of available radioluminescent light sources (e.g. GTLS) allows for implantation of the implantable phototherapy eye device within the eye or on top of the eye under the eyelid. GTLS can emit sufficient photons to produce a retinal irradiance that has elsewhere been shown to reduce rod cell dark adaptation. A transcleral anchoring system enables an implant to be held in the sclera without causing leakage out of the eye. Several other implantation locations within the eye are also possible.

In an experiment, implantable phototherapy eye devices were implanted in rabbit eyes, demonstrating the feasibility of the devices, surgery, and therapy. The surgical implantation took approximately ten minutes from the initial incision to the final suture. This rapid implantation is enabled by the disclosed anchoring system, which does not necessitate suture anchoring and self-seals the incision using its intraocular gasket.

In various embodiments of the present disclosure, wearable phototherapeutic contact lenses contain one or more light sources (e.g., a plurality of radioluminescent light sources). When worn, such contact lenses provide the treatment and prevention of ocular pathologies arising from hypoxia. The wearable phototherapeutic contact lenses remove the need for surgical implantation. This allows nightly insertion of the contact lenses for nighttime use.

In an example, a wearable phototherapeutic contact lens includes medical grade PDMS (MED-4210) that forms a lens. Embedded in the lens is a ring of twenty-four radially oriented gaseous tritium light sources, available from mb-microtec AG of Niederwangen, Switzerland. The embedding can be achieved through a two part molding process. The light sources possess a twelve-year half-life and do not emit any ionizing radiation, making them remarkably safe and reliable. The minute profile of the light sources (300 μm (1.2×10$^{-2}$ inch) diameter×2000 μm (7.9×10$^{-2}$ inch)) enables a 500 μm (2×10$^{-2}$ inch) thin contact lens suitable for comfortable overnight use. Their peak emission wavelength of 530 nm (2.09×10$^{-5}$ inch) efficiently stimulates rod cells (peak 498 nm (1.96×10$^{-5}$ inch) absorbance). Further, the annular arrangement of light sources in the lens provides an unobstructed view during photopic vision when the pupil is contracted (less than 3 mm (0.12 inch) diameter), while directing the complete phototherapeutic dose through the dilated pupil (larger than 7 mm (0.27 inch) diameter) under scotopic vision or sleep. Relative comfort of the lens and observation of the Troxler effect is possible.

In another example, a wearable phototherapeutic contact lens contains a phosphorescent pigment. The lens can includes a polymer blended with the pigment and cast into the correct lens geometry. For instance, the lens is made by combining PDMS and europium doped silicate-aluminate oxide phosphorescent pigment provided by Glow Inc. of San Francisco, Calif. The pigment has a duration rating of nine hours, although the intensity of the light emission decays over this time period. The emission peak wavelength of the pigment (approximately 505 nm ($2 \times 10^{-5}$ inch) substantially matches the peak absorbance of rod cells (approximately 500 nm ($1.97 \times 10^{-5}$ inch)).

Additionally, the compact size of the radioactive light source provides the opportunity to combine it with other optical implants (e.g. intraocular lens, glaucoma drainage devices, oxygen transporters, contact lenses). Light therapy is known to be beneficial in many conditions and synergy between the light source and the other optical implant could arise.

Embodiments related to an implantable phototherapy eye device are illustrated in FIGS. 1-19. In the interest of brevity, this device is referred to as an implantable device. Embodiments related to a wearable phototherapeutic contact lens are illustrated in FIGS. 20-24. In the interest of brevity, this phototherapy eye device is referred to as a contact lens. Generally, the implantable device is available for implantation in an eye of a subject. The implantation can occur at various placements locations in the eye. Further, more than one implantable device can be implanted in the eye. Similarly, one or more implantable devices can be implanted in the other eye of the subject as applicable and needed. Likewise, the contact lens is available to be worn on the cornea of an eye of a subject. The contact lens can be worn independently or in conjunction with an implanted phototherapy eye device. Similarly, another contact lens can be worn on the other eye of the subject as applicable and needed.

FIG. 1 illustrates an example of an implantable phototherapy eye device 100, according to embodiments of the present disclosure. The implantable device 100 includes a plurality of components. Some of the components provide a light source. Other components provide anchoring of the implantable device to a location on or in an eyeball. Yet other components provide a seal that prevents leakage of fluid from the inside of the eyeball.

In the illustrative example of FIG. 1, the implantable device 100 provides long term temporally invariant illumination to a retina of an eyeball. To do so, the implantable device 100 includes three components: a light source 110, an anchor 120, and a gasket 130. The use of these three components render the implantable device 100 to be suitable for implantation in various locations in the eye, such as in the case of transcleral and intravitreal implantations.

The light source 110 emits light having a particular wavelength and providing a therapeutic irradiance on the retina. In an example, the light source 110 is a radioluminescent light source that includes radioisotope and phosphor material(s). The materials and the dimension and geometry of the light source 110 enables the wavelength to be in the range of $1.57 \times 10^{-5}$ to $2.36 \times 10^{-5}$ inch (400 to 600 nm) and the irradiance to be substantially $10^9$ to $10^{11}$ photons/s/cm$^2$ on the retina of a human subject. Examples of the configuration of the light source 110 are further described in connection with FIG. 3.

The anchor 120 is coupled with the light source 110 and includes an anchoring surface that is mountable to a surface of an eye tissue. In particular, the anchor 120 can be bonded to the light source 110 and its anchoring surface allows retention of the light source 110 to the eye tissue once implanted. For example, the light source 110 is bonded to a portion (e.g., the center) of the retention surface. Edges of the retention surface can be sutured to the eye tissue. They can also be covered by the conjunctiva. Examples of the configuration of the anchor 120 and its coupling with the light source 110 are further described in connection with FIGS. 9-12.

The gasket 130 is coupled with the light source 110 and the anchor 120 and provides a seal that prevents leakage of fluid from the inside of the eyeball. In particular, the gasket 130 includes a fluid impermeable surface. A hole within that surface exists and is traversed by the light source 110. The hole is sealed with a biocompatible sealant material (e.g., PDMS) such that the gasket 130 is bonded to the light source 110. Areas of the surface also contact the anchor 120 and can be bonded thereto with PDMS. Examples of the configuration of the gasket 130 and its coupling with the light source 110 and the anchor 120 are further described in connection with FIGS. 5-8.

Although also suitable for other implantation locations (e.g., such as in the case of intracapsular and subchoroidal), a different configuration of the implantable device 100 can be used. For instance, for intracapsular implantation, the implantable device 100 can include the light source 110 but not the anchor 120 and/or the gasket 130. Instead, implantable light device 100 can be attached (e.g., the light source 110 bonded to an exterior surface) of an implantable lens suitable for implantation inside the lens capsule of the eyeball. Similarly and for subchoroidal implantation, the implantable device 100 can include the light source 110 but not the anchor 120 and/or the gasket 130. In this case, the implantable device 100 can be implanted by the macula lutea and eye tissue between the sclera and the choroid can retain the implantable device 100 in place.

Figure 2:
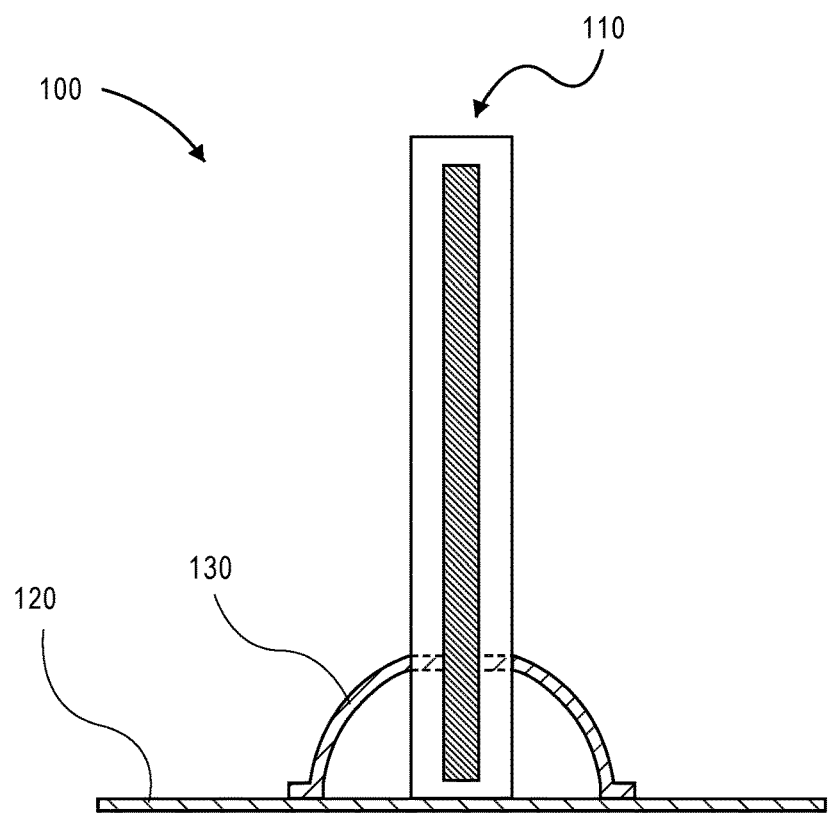
FIG. 2 illustrates a side view of the implantable phototherapy eye device of FIG. 1, according to embodiments of the present disclosure.

FIG. 2 illustrates a side view of the implantable phototherapy eye device 100 of FIG. 1, according to embodiments of the present disclosure. As shown in FIG. 2, the light source 110 sits on top and about the center of the anchoring surface of the anchor 120. For example, the bottom surface of the light source 110 and the center of the anchoring surface of the anchor 120 can be bonded with a biocompatible bonding materials, such as PDMS. Further, the light source 110 goes through a hole in the gasket 130. The hole can be filled with PDMS to bond the gasket 130 to the light source 130. The gasket 130 also sits on the attachment surface of the anchor 120.

Figure 3:
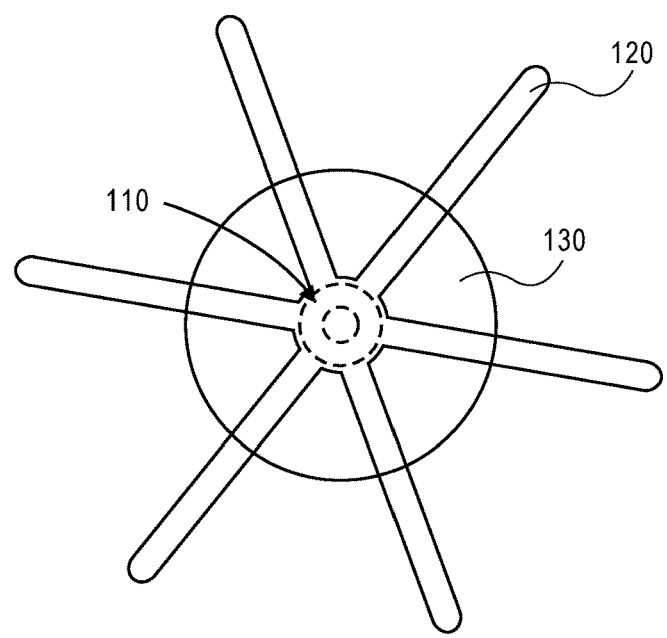
FIG. 3 illustrates a bottom view of the implantable phototherapy eye device of FIG. 1, according to embodiments of the present disclosure.

FIG. 3 illustrates a bottom view of the implantable phototherapy eye device 100 of FIG. 1, according to embodiments of the present disclosure. As shown in FIG. 3, each of the light source 110 and gasket 130 is substantially centered relative to the anchor 120. For example, the bottom surface of the light source 110 sits on top of the center of the anchoring surface of the anchor 120. Similarly, a bottom portion of the gasket 130 sits on top of the anchoring surface, goes around the center, and encircles the bottom surface of the light source 110.

Figure 4:
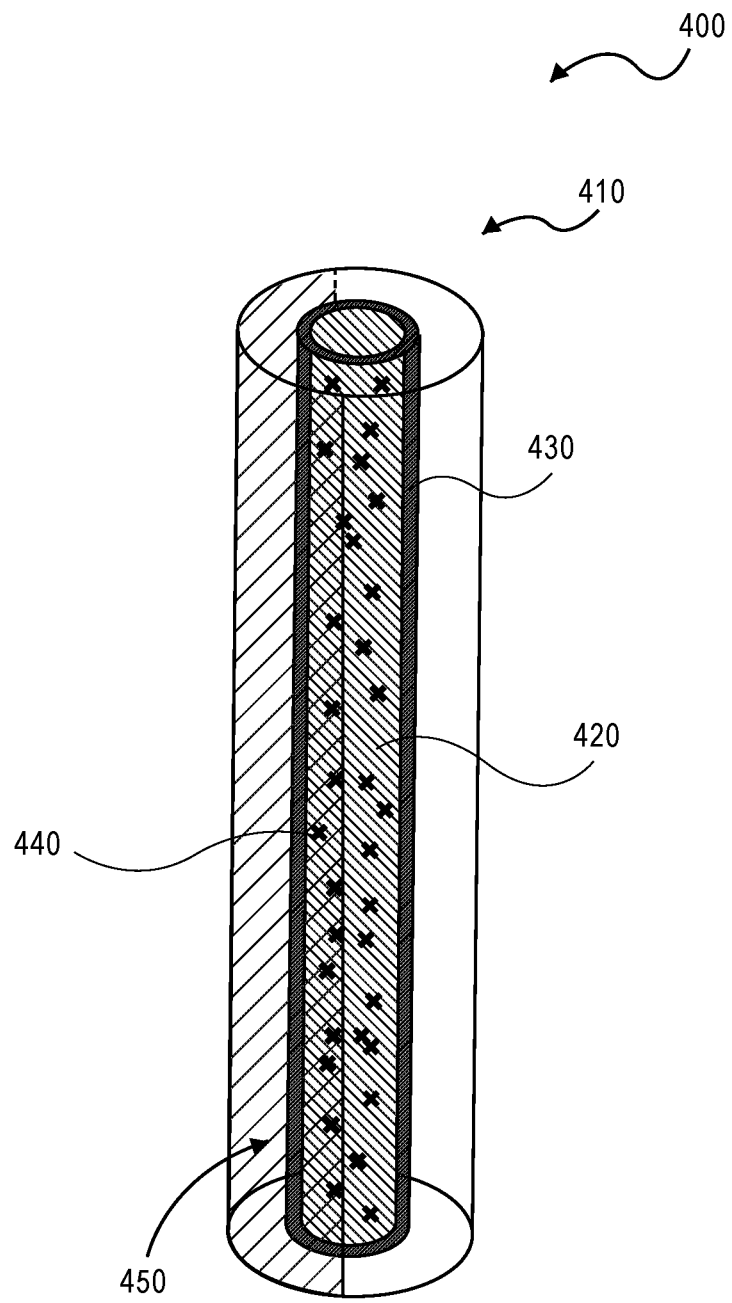
FIG. 4 illustrates an example of a light source that belongs to an implantable phototherapy eye device, according to embodiments of the present disclosure.

FIG. 4 illustrates an example of a light source 400 that belongs to an implantable phototherapy eye device, according to embodiments of the present disclosure. Some or all of the components of the light source 400 correspond to the components of the light source 110 of FIG. 1. Generally, the light source 400 is implantable, partially or fully, inside an eyeball and emits light at a particular wavelength and irradiance.

As illustrated, the light source 400 is radioluminescent light source that is made out of a light-transparent and biocompatible material (e.g., a material that is biocompatible and that light can pass through), such as glass. In another example, the radioluminescent light source may be made of a light-transparent material that may not necessarily be biocompatible. In this case, the exterior surface of the radioluminescent light source can be coated with a light-transparent and biocompatible material such as with a thin layer (between 10 micrometer and 50 micrometer) of parylene C. In both examples, the light source 400 is a biocompatible light source that can be safely implanted in an eyeball.

The shape and volume of the radioluminescent light source is defined by one or more walls 410. For instance, in the case of a cylindrical shape, the radioluminescent light source 400 includes three walls 410: a top wall and a bottom wall that form the bases of the cylinder, and a lateral wall connected to the bases. The walls 410 form a chamber 420 that is internal to the light source 400. The interior surface of one or more of the walls 410 (e.g., of the lateral wall) are coated with a phosphor material 430, such as zinc sulfide. The chamber 420 is hermetically sealed contains a radioisotope material 440 such as a gaseous tritium or solid radium. In this way, the radioisotope material 440 is subject to radioactive decay and emits ionizing radiation that collides with the phosphor material 430, thereby exciting an electron to a higher energy stage. The electron returns to its ground state releasing a photon in the process.

Further, the wall(s) 410 have a thickness and, thus, define an exterior volume of the light source 400. In an example, a portion of the exterior surface of one or more of the walls 410 (e.g., less than half of the lateral wall) is coated with a light-reflective and biocompatible material 450, such as gold, platinum, titanium, cobalt-chromium. This reflective coating increases the light transmission efficiency of the light source by reflecting photons in one direction (e.g., by doubling the irradiance through the uncoated exterior surface when the reflective material 450 covers half of the exterior surface). Other surfaces of the light source 400 can additionally or alternatively be coated with a light-reflective and biocompatible material. For example, an internal surface between the exterior surface and the chamber can be coated. Further, the light source 400 can include a second chamber that encapsulates the other chamber (the one containing the radioisotope material). Surfaces of that second chamber can be coated.

The exterior surface can also be coated with a transparent biocompatible material that protects the light source 400 from biological elements in the eyeball. Accordingly, this protective coating increases the life of the implanted light source 400. In an example, a thin layer of parylene C, less than one millimeter thick (e.g., about thirty micrometer), can be deposited on the exterior surface of the walls 410.

The volume, shape, and coating(s) (e.g., internal coating with phosphor material and external coating with light-reflective material) can control the wavelength and irradiance of the emitted light. Different volumes, shapes, and/or coating(s) are possible. In an example, the exterior volume is in range of $6.1 \times 10^{-5}$ to $6.1 \times 10^{-2}$ cubic inch (1 to 1000 mm³). In another example, the exterior volume is in range of $6.1 \times 10^{-5}$ to $6.1 \times 10^{-3}$ cubic inch (1 to 100 mm³). In yet another example, the exterior volume is in range of $6.1 \times 10^{-5}$ to $1.2 \times 10^{-3}$ cubic inch (1 to 20 mm³). These different exterior volumes allow suitable implantation of the light source 400 in the eyeball given that the volume of the vitreous humor is about 0.24 cubic inch (3900 mm³) for the average human eye.

Various shapes are possible, including cylindrical, rectangular, triangular, and other geometric shapes. In the example of a cylindrical shape, the cylinder has a height in the range of 0.04 to 0.79 inch (1 to 20 mm). The thickness of the lateral wall 410 is in the range of $3.9 \times 10^{-3}$ to 0.2 inch (0.1 to 0.5 mm).

The interior volume (e.g., the volume of the chamber 420) depends on the exterior volume and thickness of the walls 410. For instance, in the case of an exterior volume in the range of $6.1 \times 10^{-5}$ to $6.1 \times 10^{-3}$ cubic inch (1 to 100 mm³), the interior volume is in range of $3 \times 10^{-5}$ to $5.5 \times 10^{-3}$ cubic inch (0.5 to 90 mm³).

When zinc sulfide with certain activators (e.g. silver, aluminum, copper) is used for the internal coating and no external light-reflecting coating is applied, and when the chamber 420 contains gaseous tritium, the emitted light can have a wavelength in the range of $1.57 \times 10^{-5}$ to $2.37 \times 10^{-5}$ inch (400 nm to 600 nm) at peak emission. Strontium aluminate with certain dopants (e.g. europium, dysprosium, manganese, boron) can also achieve this range of wavelengths. This range includes the maximum absorbance of rod cells and excludes the maximum absorbance of blue and green cones.

In an illustrative example, the light source 400 is a radioluminescent light source that has a cylindrical shape. The thickness of the lateral wall 410 is about $9.8 \times 10^{-3}$ inch (0.25 mm). The chamber 420 extends across the entire lateral wall 410 (e.g., the chamber 420 ends at the top and bottom bases and has about the same height as the light source 400; the difference is that the chamber has a smaller base radius given the thickness of the walls 410). The height of the lateral wall 410 is about 0.24 inch (6 mm). The radius of the base (top or bottom) is about 0.03 inch (0.75 mm). Hence, the exterior volume is about $6.5 \times 10^{-5}$ cubic inch (10.6 mm³). The interior volume is about $2.9 \times 10^{-5}$ cubic inch (4.71 mm³). The interior surface of at least the lateral wall 410 is coated with zinc sulfide. The interior volume represented by the chamber 420 is filled with gaseous tritium. Optionally, half (in the lateral direction as shown in FIG. 4) of the exterior surface of the lateral wall is coated with a thin layer (e.g., about thirty micrometer) of gold. The entire exterior surface of the radioluminescent light source is also optionally coated with a thin parylene C layer. This protective layer can be deposited on top or below the gold coating. Absent the gold coating, the emitted light has a wavelength at peak emission of about $1.97 \times 10^{-5}$ inch (500 nm), corresponding to the maximum absorbance of rod cells. The irradiance is about $10^9$ photons/s/cm² on the retina of a human eyeball. This irradiance is sufficiently high to prevent rod hyperpolarization (and, thus, hypoxia) and low enough to prevent cone simulation. In an example, the irradiance can be expressed as a function of distance from the light source 400 based on an average size of the human eye and the distance between sclera and the retina. For instance, in a transcleral implantation, the irradiance is in the range of $10^9$ to $10^{10}$ photons/s/cm² at a distance from the light source 400, where this distance represents the distance between the location of the transcleral implantation and the retina, such as about 15 mm (059 inch).

Hence, the light source 400 is a biocompatible radioluminescent light source implantable inside an eyeball. The biocompatible radioluminescent light source includes one or more walls that form a chamber. A phosphor material coats at least one of the one or more walls. A radioisotope material is within the chamber. An exterior volume of the biocompatible radioluminescent light source is in the range of 1 mm³ to 1000 mm³.

Although FIG. 4 illustrates a radioluminescent light source, other light sources may be similarly configured and used in an implantable device. For example, walls of the light source can form one or more chambers to additionally or alternatively include one or more of light emitting diode(s), electroluminescent source(s), chemiluminescent source(s), electrochemiluminescent source(s), bioluminescent source(s), phosphorescent source(s), fluorescent source(s), and upconverting crystal(s).

Figure 5:
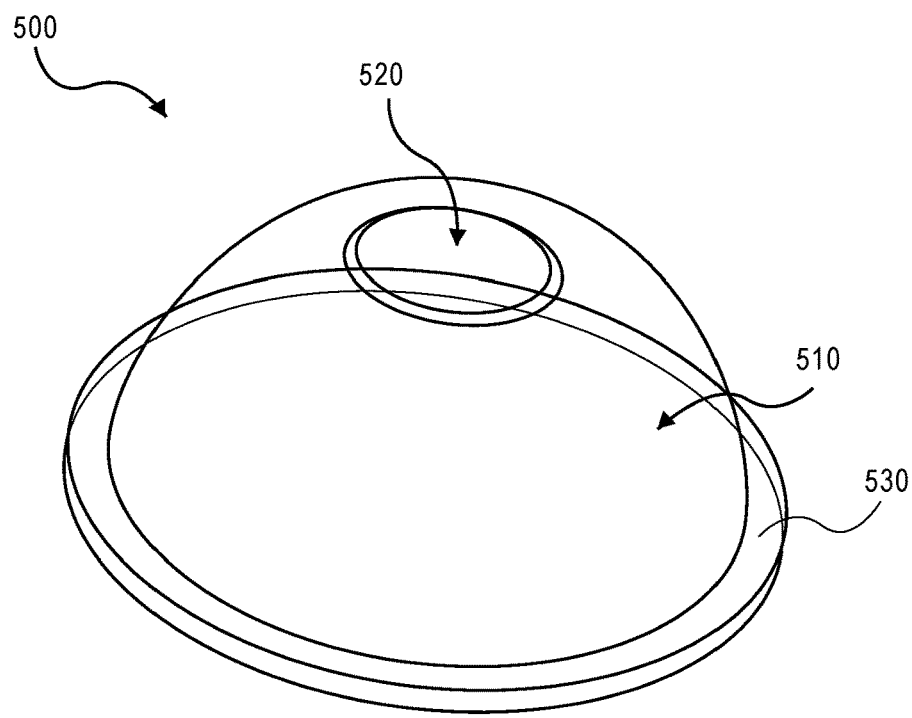
FIG. 5 illustrates an example of a gasket that belongs to an implantable phototherapy eye device, according to embodiments of the present disclosure.

FIG. 5 illustrates an example of a gasket 500 that belongs to an implantable phototherapy eye device, according to embodiments of the present disclosure. Some or all of the components of the gasket 500 correspond to the components of the gasket 130 of FIG. 1. Generally, the gasket 500 provides a seal such that, when the implantable device is implanted in an eyeball through an incision, fluid does not leak from inside the eyeball through the incision. In other words, the gasket 500 represents an intraocular gasket.

As illustrated in FIG. 5, the gasket 500 is made of a flexible and biocompatible material that is impermeable to the fluid. In an example, this material is PDMS (MED-4210). This material is shaped in a hemispherical dome shape (e.g., a hemispherical dome, or half of a sphere) in an uncompressed state (or partially compressed state) to form a skirt 510.

The skirt 510 includes a hole 520. This hole 520 can be located substantially at a top of the hemispherical dome shape (e.g., the top of the skirt 510). The radius of the hole 520 can be substantially the same or slightly larger than the cross section (e.g., the exterior radius of a cylindrically shaped) of a light source. In this way, the gasket 500 can receive a portion of the light source through the hole 520. Any gap between the hole 520 and the part of the light source in the hole 520 can be sealed with a sealant material. In particular, biocompatible and sealant material can be applied around the light source at the location of the hole 520. Further, the sealant material can act as a bonding material. For example, PDMS (MED-4210) can be used for the sealing and bonding.

In an example, the skirt 510 also includes a lip 530. This lip 530 can be at the bottom of the hemispherical dome shape (e.g., the bottom of the skirt 510, opposite to the hole 520). The lip 530 can have a width that provides a surface for attaching the skirt 510 (and, equivalently, the gasket 500) to an anchor. For example, the lip 530 sits on top of an attachment surface of the anchor and can be bonded thereto with PDMS (MED-4210).

Hence, the gasket 500 can receive the light source through the hole 520. The skirt 530 can also attach the gasket 500 to the anchor. In this way, a portion of the light source is disposed in the gasket 500 (when the gasket is in an uncompressed or partially compressed state). An end of the light source (e.g., the bottom base of a cylindrically shaped light source) is attached to the anchor. A portion of the body of the light source extends outwardly from the end and traverses the hole 520. Upon implantation, the gasket 500 can be compressed. However, the hole 520 is sealed, thereby preventing fluid leakage.

In an example, the light source has a cylindrical shape with an exterior radius of about $2.95 \times 10^{-2}$ inch (0.75 mm). The hole 520 is radius of the hole is slightly larger by one to 5 percent than this exterior radius of the cylinder. The radius of the bottom surface of skirt 510 (e.g., the opposite surface relative to the hole 520) is about 0.12 inch (3 mm). The height of the spherical dome (e.g., between the bottom surface and the hole 520) is about 0.05 inch (1.33 mm). The height of the portion of the light source disposed in the gasket 500 is substantially the same as this height (e.g., about 0.05 inch (1.33 mm)). The width of the lip 530 is about $5 \times 10^{-3}$ inch (0.1 mm). The thickness of the PDMS material used to form the skirt 510 is also about $5 \times 10^{-3}$ inch (0.1 mm).

Figure 6:
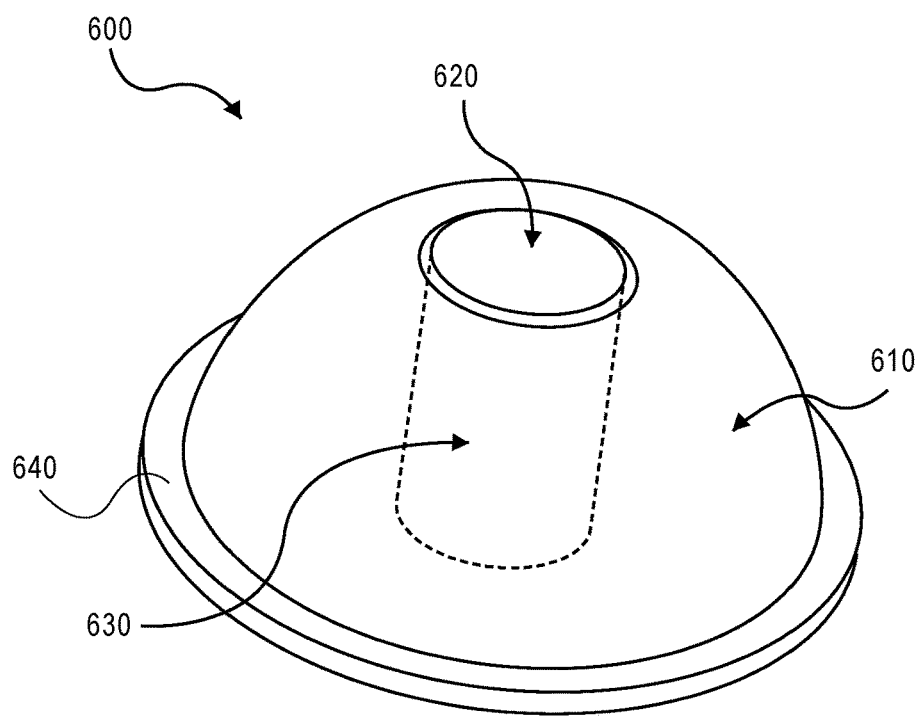
FIG. 6 illustrates another example of a gasket that belongs to an implantable phototherapy eye device, according to embodiments of the present disclosure.

FIG. 6 illustrates another example of a gasket 600 that belongs to an implantable phototherapy eye device, according to embodiments of the present disclosure. Some or all of the components of the gasket 600 correspond to the components of the gasket 130 of FIG. 1. Unlike the gasket 500 of FIG. 5, the body of the gasket 600 is not hollow. Instead, the gasket 600 includes a hemispherical dome body 610 that is made of a biocompatible material that can be flexible, such as PDMS (MED-4210). This body 610 (shaped in a hemispherical dome) includes an attachment cavity 630 that extends inward from a hole 620 located substantially at a top of the hemispherical dome body 610. At the opposite end relative to the hole 620 (e.g., at the bottom), the hemispherical dome body 610 include a lip 640 for attachment to an anchor.

In an example, the attachment cavity 630 extends from the hole 620 to the bottom of the hemispherical dome body 610. In an example, the attachment cavity 630 extends from the hole 620 to a particular location within the hemispherical dome body 610 (e.g., to halfway). In either examples, the attachment cavity 630 receives a portion of a light source through the hole 620 and can be bonded thereto such that the light source is securely attached to and retained in the gasket 600.

Figure 7:
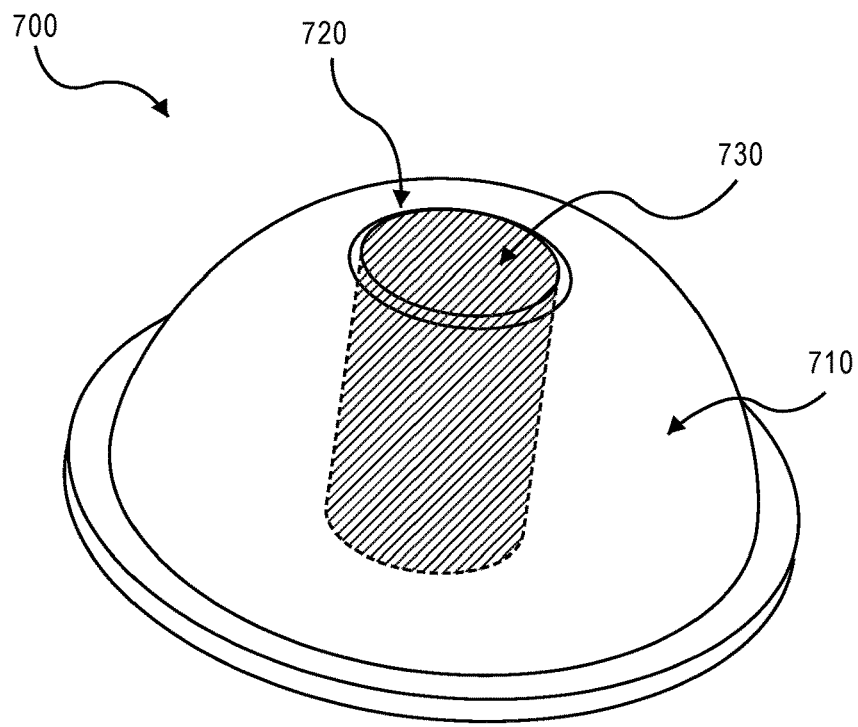
FIG. 7 illustrates yet another example of a gasket that belongs to an implantable phototherapy eye device, according to embodiments of the present disclosure.

FIG. 7 illustrates yet another example of a gasket 700 that belongs to an implantable phototherapy eye device, according to embodiments of the present disclosure. Some or all of the components of the gasket 700 correspond to the components of the gasket 130 of FIG. 1. Similarly to the gasket 600 of FIG. 6, the gasket 700 includes a hemispherical dome body 710 having a hole 720 and an attachment cavity. However, a solid piece 730, such as a solid glass piece, is placed and retained in the attachment cavity and occupies, fully or partially, this cavity. An end of the solid piece 730 is exposed to hole 730. In an example, the exposed end can be located within the attachment cavity such that this end is within the hemispherical dome body 710. In another example, the solid piece 730 protrudes the hemispherical dome body 710 through the hole 520 such that the exposed end is outside of the hemispherical dome body 710. In both example, the exposed end can be attached (e.g. bonded) with an end of a light source such that the light source is securely attached to and retained by the gasket 700.

Figure 8:
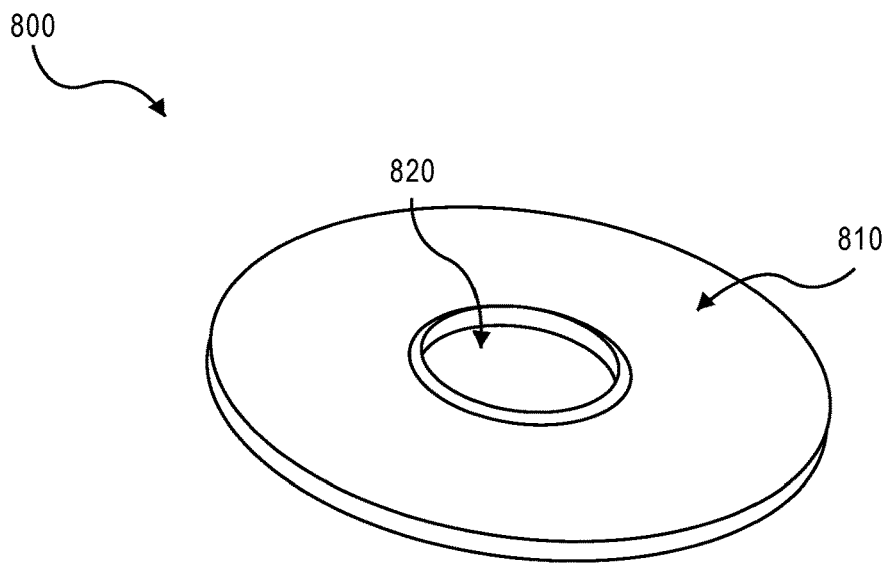
FIG. 8 illustrates a further example of a gasket that belongs to an implantable phototherapy eye device, according to embodiments of the present disclosure.

FIG. 8 illustrates a further example of a gasket 800 that belongs to an implantable phototherapy eye device, according to embodiments of the present disclosure. Some or all of the components of the gasket 800 correspond to the components of the gasket 130 of FIG. 1. Unlike the gaskets 500, 600, and 700 of FIGS. 5, 6, and 7, respectively, the gasket 800 does not have a hemispherical dome shape. Instead, the gasket 800 includes a substantially flat disc 810 that is made of a biocompatible material that can be flexible, such as PDMS (MED-4210). The flat disc 810 includes a hole 820. In the implantable device, the flat disc 810 is located on the same side as an anchoring surface of an anchor. An end of a light source is attached to the anchoring surface of the anchor. A portion of a body of the light source is located in the hole 820.

Figure 9:
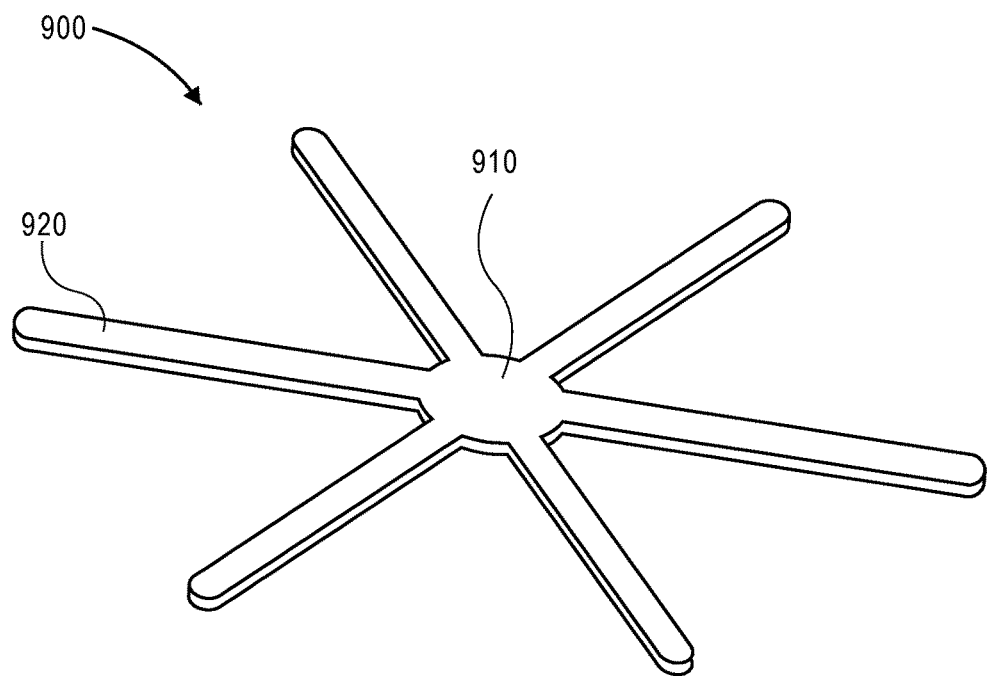
FIG. 9 illustrates an example of an anchor that belongs to an implantable phototherapy eye device, according to embodiments of the present disclosure.

FIG. 9 illustrates an example of an anchor 900 that belongs to an implantable phototherapy eye device, according to embodiments of the present disclosure. Some or all of the components of the anchor 900 correspond to the components of the anchor 120 of FIG. 1. Generally, the anchor 900 can be an ocular anchor that includes an anchoring surface mountable to an eye tissue (e.g., to a surface of the eye tissue). When the implantable device is implanted in an eyeball, the attachment surface is secured to a part of the eyeball (e.g., to a tissue or some surface of the eyeball).

As illustrated in FIG. 9, the anchor 900 is made of a flexible and biocompatible material. In an example, this material is PDMS (MED-4210). This material is shaped to form a center body 910 and a plurality of arms 920 extended outwardly from the center body 910. FIG. 9 illustrates six arms 920. Nonetheless, a different number of arms 920 is possible. Generally, an end of the light source is attached to the center body 920. For example, that end sits on a surface of the center body, and the surface is bonded to the end of the light source. That same surface on the arms 920 correspond to the attachment surface used to secure the implantable device in place, once implanted.

In an example, the center body 910 has a same cross section as the one of the end of the light source. For instance, in the case of a cylindrically shaped light source, the end is a bottom base of the cylinder. Accordingly, the surface of the center body 910 is shaped as a circle. The radius of the surface can also correspond to (e.g. be equal to or slightly larger than) the radius of the bottom base. Alternatively, the surface radius is a function of the bottom base radius (e.g., twenty-five percent larger). Regardless, the end of the light source generally sits and is centered around the center of the center body 910.

The arms 920 can be distributed around the center body 910. In an example, a particular distribution pattern is achieved (e.g., the arms are evenly distributed and forms pairs, where arms in a pair are opposite of each other). Generally, the arms 920 are made of a flexible and biocompatible material. This material is folded in a packaged state of the implantable device and is extended in a implanted state of the implantable device. In other words, when packaged, the arms are folded 920 and allow easy insertion of the implantable phototherapy eye in a syringe for implantation. Once implanted in the eyeball, the arms 920 can be extended to secure the implantable phototherapy eye in place.

In an illustrative example, the center body 910 is circular and has a radius of about 0.03 inch (0.75 mm). Each of the arms has a length of about 0.2 inch (5.25 mm). The thickness of the PDMS material used to form the anchor 900 is also about $5 \times 10^{-3}$ inch (0.1 mm).

Figure 10:
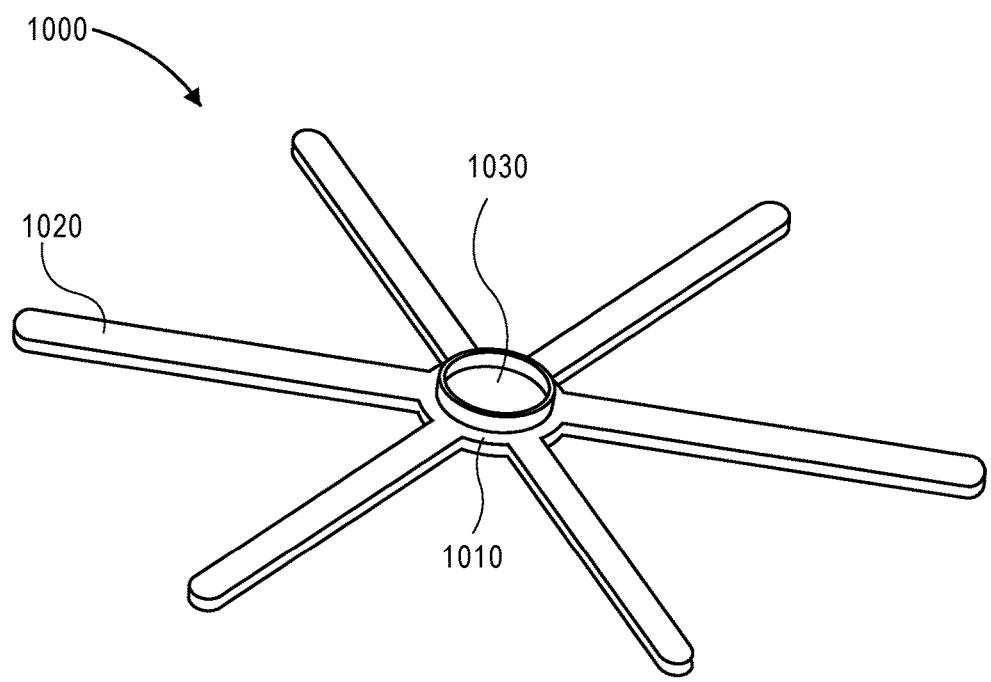
FIG. 10 illustrates another example of an anchor that belongs to an implantable phototherapy eye device, according to embodiments of the present disclosure.

FIG. 10 illustrates another example of an anchor 1000 that belongs to an implantable phototherapy eye device, according to embodiments of the present disclosure. Some or all of the components of the anchor 1000 correspond to the components of the anchor 120 of FIG. 1. Similarly to the anchor 900 of FIG. 9, the anchor 1000 includes a center body 1010 and a plurality of arms 1020. However, instead of having a flat surface 1010 to receive an end of a light source, the center body 1010 includes one or more walls that form a cavity 1030. In the implantable phototherapy eye, the end of the light source is disposed in the cavity 1030. The bottom and the wall(s) of the cavity 1030 can be bonded to the light source to provide secure attachment. In an example, a lateral wall is used to form a cylindrical cavity 1030. The height of this lateral wall is a function of the radius of the cavity 1030 (e.g., fifty percent). The thickness of the wall can be the same as the thickness of the anchor 1000 (e.g., about $5 \times 10^{-3}$ inch (0.1 mm)).

Figure 11:
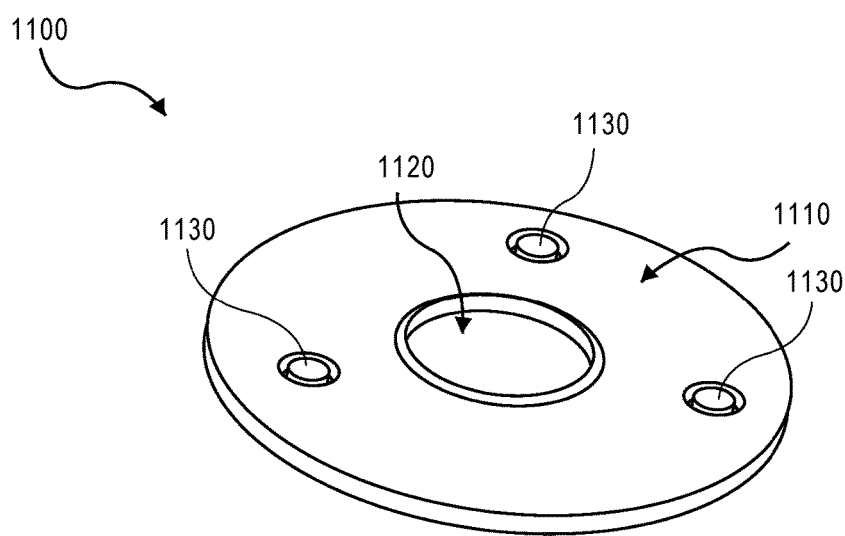
FIG. 11 illustrates yet another example of an anchor that belongs to an implantable phototherapy eye device, according to embodiments of the present disclosure.

FIG. 11 illustrates yet another example of an anchor 1100 that belongs to an implantable phototherapy eye device, according to embodiments of the present disclosure. Some or all of the components of the anchor 1100 correspond to the components of the anchor 120 of FIG. 1. Unlike the anchors 900 and 1000 of FIGS. 9 and 10, respectively, the anchor 1100 does not include arms. Instead, the anchor 1100 includes a flexible and biocompatible plate 1110. This plate 1110 can be made out of a flexible and biocompatible material, such as PDMS (MED-4210). The center of the plate 1110 may be flat, may include one or more walls that define a cavity, or as illustrated in FIG. 11, contain a hole 1120. As such, the center of the plate 1110 generally receives and is attached to an end of a light source. For example, in the case of a cylindrically shaped light source, the hole 1120 has a radius that is equal or slightly larger than the one of the bottom base of the cylinder. Any gap between the hole 1120 and the light source can be bonded. Further, the plate 1110 can include one or more anchoring holes 1130. These holes 1130 are used, for example, to suture the plate 1110 to an eye tissue or surface.

In an illustrative example, the plate 1110 is circular and has a radius of about 0.12 inch (3 mm). Each of the holes has a radius of about $5 \times 10^{-3}$ inch (0.1 mm). The thickness of the PDMS material used to form the anchor 1100 is also about $5 \times 10^{-3}$ inch (0.1 mm).

Figure 12:
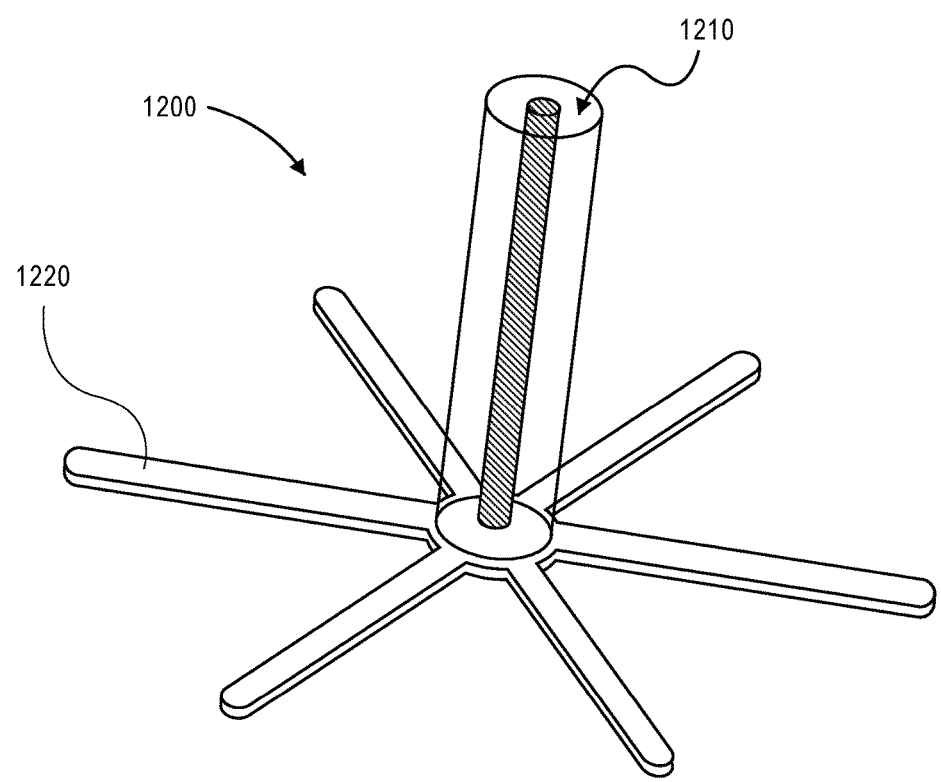
FIG. 12 illustrates another example of an implantable phototherapy eye device, according to embodiments of the present disclosure.

FIG. 12 illustrates another example of an implantable phototherapy eye device 1200, according to embodiments of the present disclosure. Unlike the implantable device 100 of FIG. 1, the implantable device 1200 does not include a gasket. Instead, the implantable device 1200 includes a light source 1210 and an anchor 1220. The light source 1210 is coupled with the anchor 1220. For example, an end of the light source 1210 is bonded with a surface of the center body of the anchor 1220.

In an example, the light source 1210 includes some or all of the components of the light source 400. For instance, the light source 1210 is a cylindrically shaped radioluminescent light source that contains a chamber internally coated with zinc sulfide and retaining gaseous tritium.

As illustrated in FIG. 12, the anchor 1220 is similar to the anchor 900 of FIG. 9 and includes a center body and a plurality of arms. However, the implantable device 1200 can use instead any of anchors 1000 or 1100 of FIGS. 10 and 11, respectively.

While the implantable device 100 of FIG. 1 prevents fluid leakage when implanted, such prevention may not be provided by the implantable device 1200 of FIG. 12 because this device 1200 lacks a gasket. However, the implantable device 1200 can be relatively simpler to manufacturer and to implant. Because fluid leakage is not prevented, the implantable device 1200 may be used for intravitreal or subchoroidal implantations rather than transcleral implantation. For transcleral implantation, the implantable device 100 may be used because it prevent fluid leakage from inside an eyeball to the outside surface of the sclera.

Figure 13:
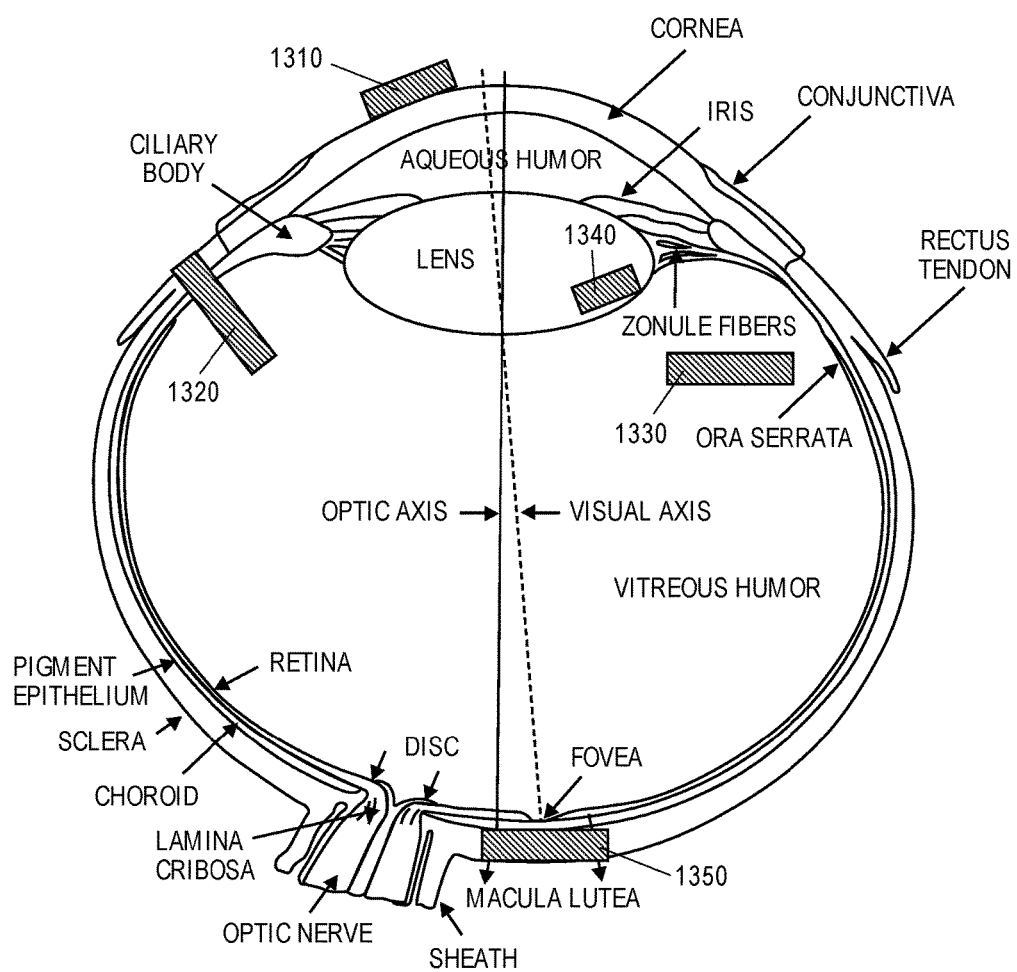
FIG. 13 illustrates placement options for a phototherapy eye device, according to embodiments of the present disclosure.

FIG. 13 illustrates placement options for a phototherapy eye device, according to embodiments of the present disclosure. Generally, the placement options include supercorneal 1310, transcleral 1320, intravitreal 1330, intracapsular 1340, and subchoirodal 1350. The use of each of the placement options depends on the configuration of the phototherapy eye device.

In an example, the supercorneal placement 1310 corresponds to placing the phototherapy eye device on the outside surface of the cornea of an eyeball. This placement 1310 is suitable for use with a contact lens (the configuration of which is further illustrated in the next figures).

The transcleral placement 1320 corresponds to implanting the phototherapy eye device through the sclera and choroid of the eyeball and anchoring this device to the outside surface of the sclera. This placement 1320 is suitable for use with an implantable device that includes a light source, an anchor, and a gasket, such as the implantable device 100 of FIG. 1 or any implantable device that contains a combination of one or more light sources 400 of FIG. 4, one or more of the gaskets 500-800 of FIGS. 5-8, and one or more anchors 900-1100 of FIGS. 9-11. The light source(s) is inserted inside the eyeball via an incision through the sclera and choroid. Only a small portion of the light source is occluded by the eye tissues of the sclera and choroid. The gasket is inside the eyeball and contacts the inside surface of the choroid. The anchor contacts on the outside surface of the sclera.

The intravitreal placement 1330 corresponds to implanting the phototherapy eye device through the sclera and choroid of the eyeball and anchoring this device to the inside surface of the choroid. This placement 1330 is suitable for use with an implantable device that includes a light source and an anchor but not necessarily a gasket, such as the implantable device 1200 of FIG. 12 or any implantable device that contains a combination of one or more light sources 400 of FIG. 4 and one or more anchors 900-1100 of FIGS. 9-11. The light source(s) is inserted and sits completely inside the eyeball via an incision through the sclera and choroid. No portion of the light source is occluded by the eye tissues of the sclera and choroid. The anchor contacts the inside surface of the choroid.

The intracapsular placement 1340 corresponds to implanting the phototherapy eye device inside the lens capsule of the eyeball. This placement 1340 is suitable for use with an implantable device that includes a light source but not necessarily an anchor or a gasket, such as any implantable device that contains one or more light sources 400 of FIG. 4. The light source(s) can be attached to an implantable intraocular lens.

The suprachoroidal placement 1350 corresponds to implanting the phototherapy eye device completely between the sclera and choroid by the macula lutea. This placement 1350 is suitable for use with an implantable device that includes a light source but not necessarily an anchor or a gasket, such as any implantable device that contains one or more light sources 400 of FIG. 4. The light source(s) can be retained in place by the eye tissue. Optionally, the implantable device can also include an anchor to further secure it in place. The device may also be implanted epiretinally.

Figure 14:
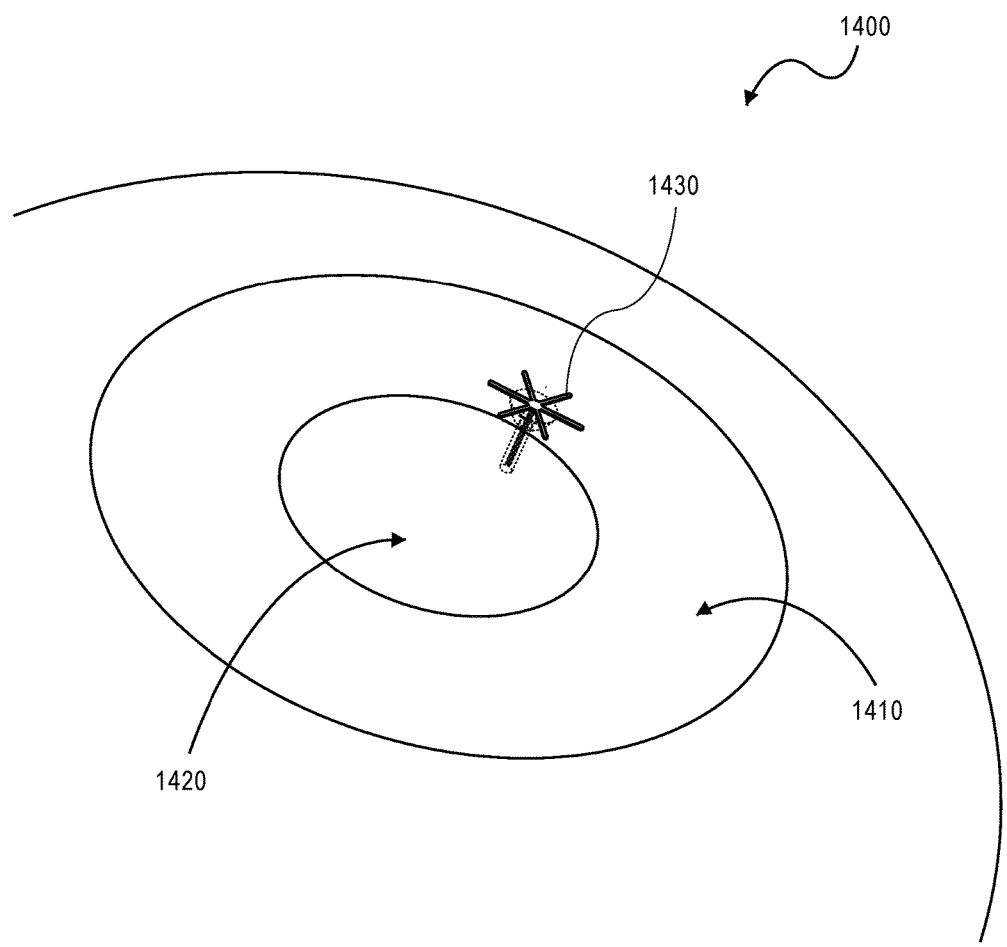
FIG. 14 illustrates an example of a transcleral implantation of a phototherapy eye device, according to embodiments of the present disclosure.

FIG. 14 illustrates an example of a transcleral implantation 1400 of a phototherapy eye device, according to embodiments of the present disclosure. As illustrated, an eyeball includes a sclera 1410 and a cornea 1420. A light source of an implantable device 1430 is inserted inside the eyeball via an incision in the sclera 1410 and not the cornea 1420. An anchor of the implantable device 1430 is secured to the outside surface of the sclera. For example, the attachment surface of the anchor is in direct contact with the outside surface of the sclera. The anchor can be covered with the conjunctiva using suture.

Figure 15:
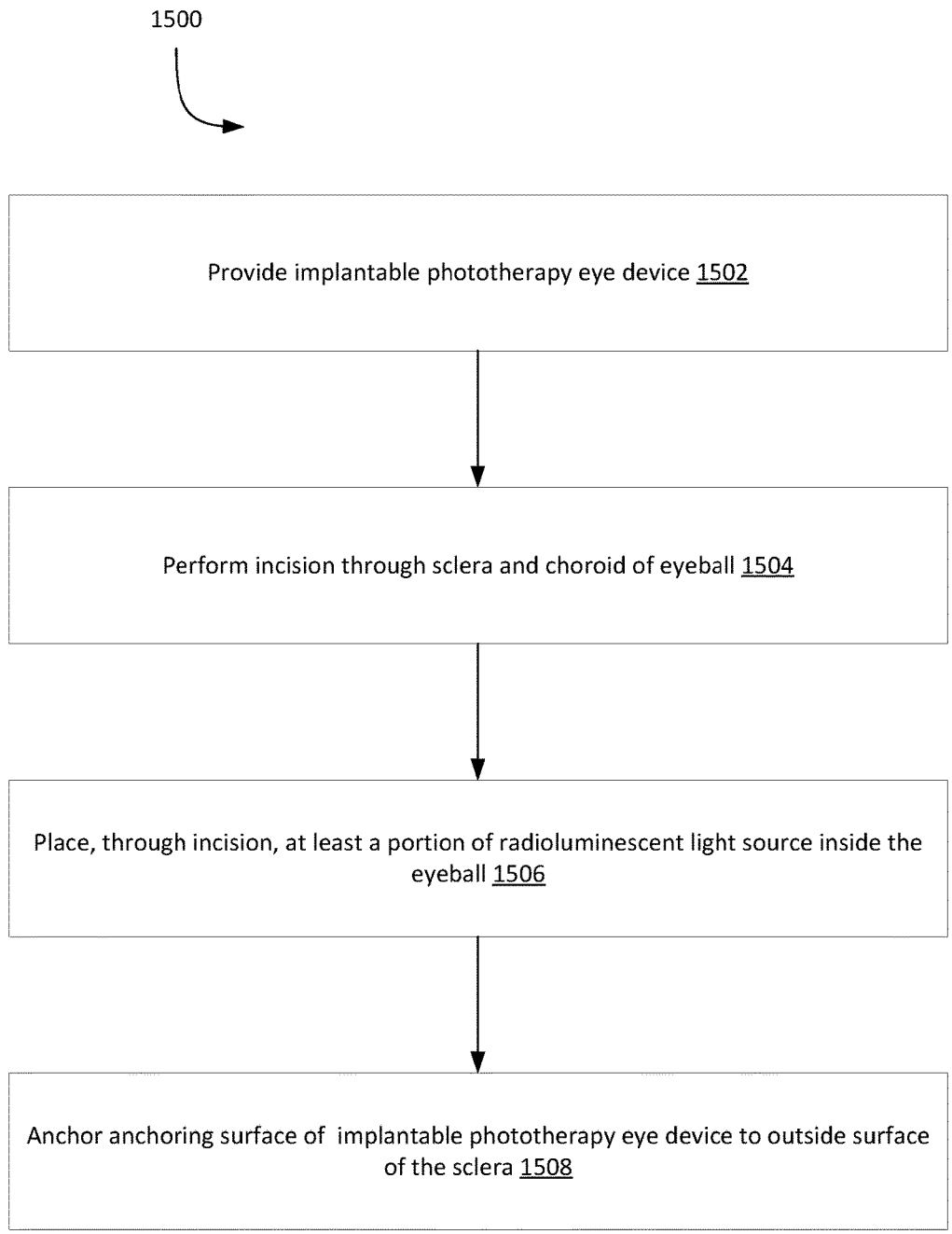
FIG. 15 illustrates an example of a flow for a transcleral implantation of a phototherapy eye device, according to embodiments of the present disclosure.

FIG. 15 illustrates an example of a flow 1500 for a transcleral implantation of a phototherapy eye device, according to embodiments of the present disclosure. The flow 1500 can be performed by a trained medical practitioner.

The flow 1500 starts at step 1502, where an implantable phototherapy eye device is provided. For example, the medical practitioner can directly or indirectly obtain the implantable phototherapy eye device from a seller or manufacturer of such devices. The implantable phototherapy eye device includes a light source, an anchor, and a gasket, such as the implantable device 100 of FIG. 1 or any implantable device that contains a combination of one or more light sources 400 of FIG. 4, one or more of the gaskets 500-800 of FIGS. 5-8, and one or more anchors 900-1100 of FIGS. 9-11. The implantable phototherapy eye device can be provided or placed in a syringe or instrument to assist with insertion.

At step 1504, an incision is performed through the sclera and choroid of an eyeball of a subject. For example, it may be desired to implant the implantable phototherapy eye device in the eyeball. The medical practitioner may prepare the subject for the implantation (e.g., provide any needed instructions and anesthesia) and may use a sharp tool, like the syringe to cut the incision.

At step 1506, at least a portion of the light source (e.g., a portion of the radioluminescent light source 400 of FIG. 4) is placed inside the eyeball through the incision. For example, the medical practitioner inserts the syringe inside the eyeball through the incision. The syringe contains the implantable phototherapy eye device in a packaged state (e.g., any arms of the anchor are folded). The anchor stays external to the outside surface of the sclera. The gasket and the light source are pushed through the incision by operating the syringe. The gasket can sit on the inner eye tissue (e.g. choroid or retina).

At step 1508, an anchoring surface of the implantable phototherapy eye device is anchored to the outside surface of the sclera. For example, the medical practitioner operates the syringe to push out and position the anchor such that its anchoring surface is in contact with the outside surface of the sclera. The syringe is then removed and the implantable device is secured in its transcleral placement.

Figure 16:
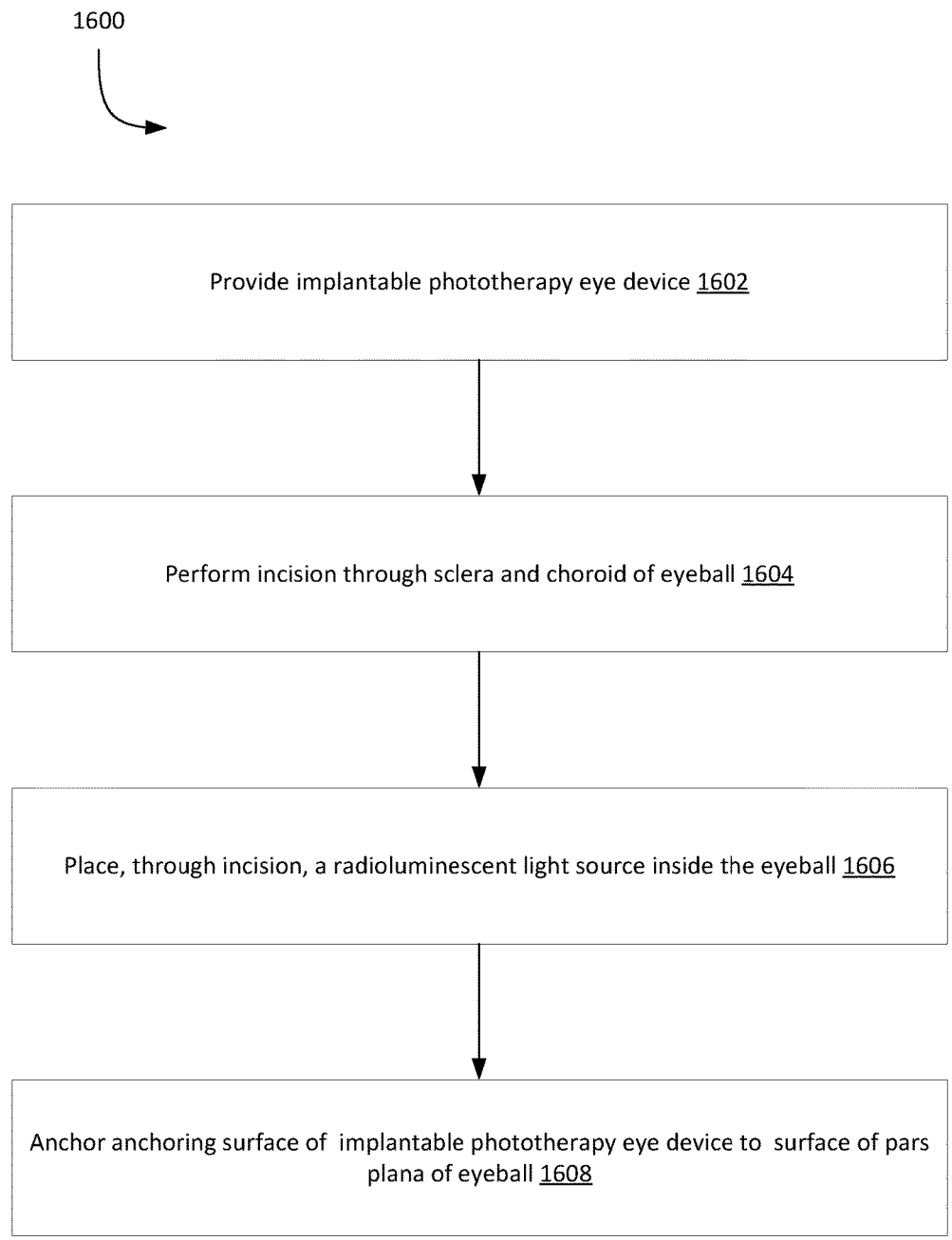
FIG. 16 illustrates an example of a flow for an intravitreal implantation of a phototherapy eye device, according to embodiments of the present disclosure.

FIG. 16 illustrates an example of a flow 1600 for an intravitreal implantation of a phototherapy eye device, according to embodiments of the present disclosure. The flow 1600 can be performed by a trained medical practitioner. Some of the steps of the flow 1600 are similar to steps of the flow 1500 of FIG. 15. The description of the similar steps is not repeated herein.

The flow 1600 starts at step 1602, where an implantable phototherapy eye device is provided. The implantable phototherapy eye device includes a light source and an anchor but not necessarily a gasket, such as the implantable device 1200 of FIG. 12 or any implantable device that contains a combination of one or more light sources 400 of FIG. 4 and one or more anchors 900-1100 of FIGS. 9-11.

At step 1604, an incision is performed through the sclera and choroid of an eyeball of a subject.

At step 1606, the light source (e.g., the radioluminescent light source 400 of FIG. 4) is placed inside the eyeball through the incision. For example, the medical practitioner inserts the syringe inside the eyeball through the incision. The syringe contains the implantable phototherapy eye device in a packaged state (e.g., any arms of the anchor are folded). The anchor and the light source are pushed through the incision by operating the syringe. The anchor can sit inside the eyeball past the choroid.

At step 1608, an anchoring surface of the implantable phototherapy eye device is anchored to the pars plana of the eyeball. For example, the medical practitioner operates the syringe to push out and position the anchor such that its anchoring surface is in contact with the pars plana. The syringe is then removed and the implantable device is secured in its intravitreal placement.

Figure 17:
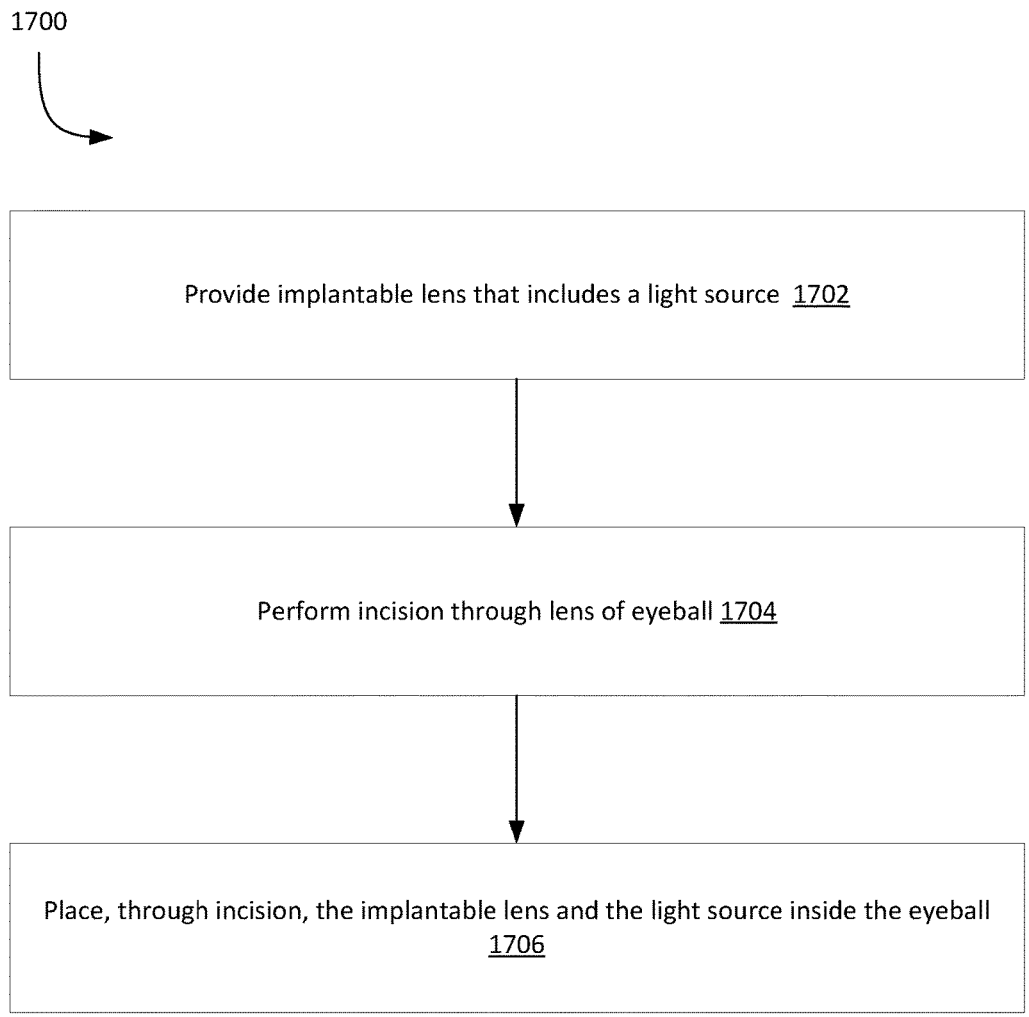
FIG. 17 illustrates an example of a flow for an intracapsular implantation of a phototherapy eye device, according to embodiments of the present disclosure.

FIG. 17 illustrates an example of a flow for an intracapsular implantation of a phototherapy eye device, according to embodiments of the present disclosure. The flow 1700 can be performed by a trained medical practitioner. Some of the steps of the flow 1700 are similar to steps of the flow 1500 of FIG. 15. The description of the similar steps is not repeated herein.

The flow 1700 starts at step 1702, where an implantable lens is provided. The implantable lens includes a light source, such as one or more of radioluminescent light sources 400 of FIG. 4, but not necessarily an anchor or a gasket. The implantable lens can be provided or placed in a syringe.

At step 1704, an incision is performed through the lens capsule of an eyeball of a subject.

At step 1706, the implantable lens and the light source (e.g., the radioluminescent light source(s) 400 of FIG. 4) are placed inside the lens capsule of the eyeball through the incision. For example, the medical practitioner inserts the syringe inside the lens capsule through the incision. The implantable lens and the light source are pushed through the incision by operating the syringe. The light source can sit completely inside the lens capsule of the eyeball in its intracapsular placement.

Figure 18:
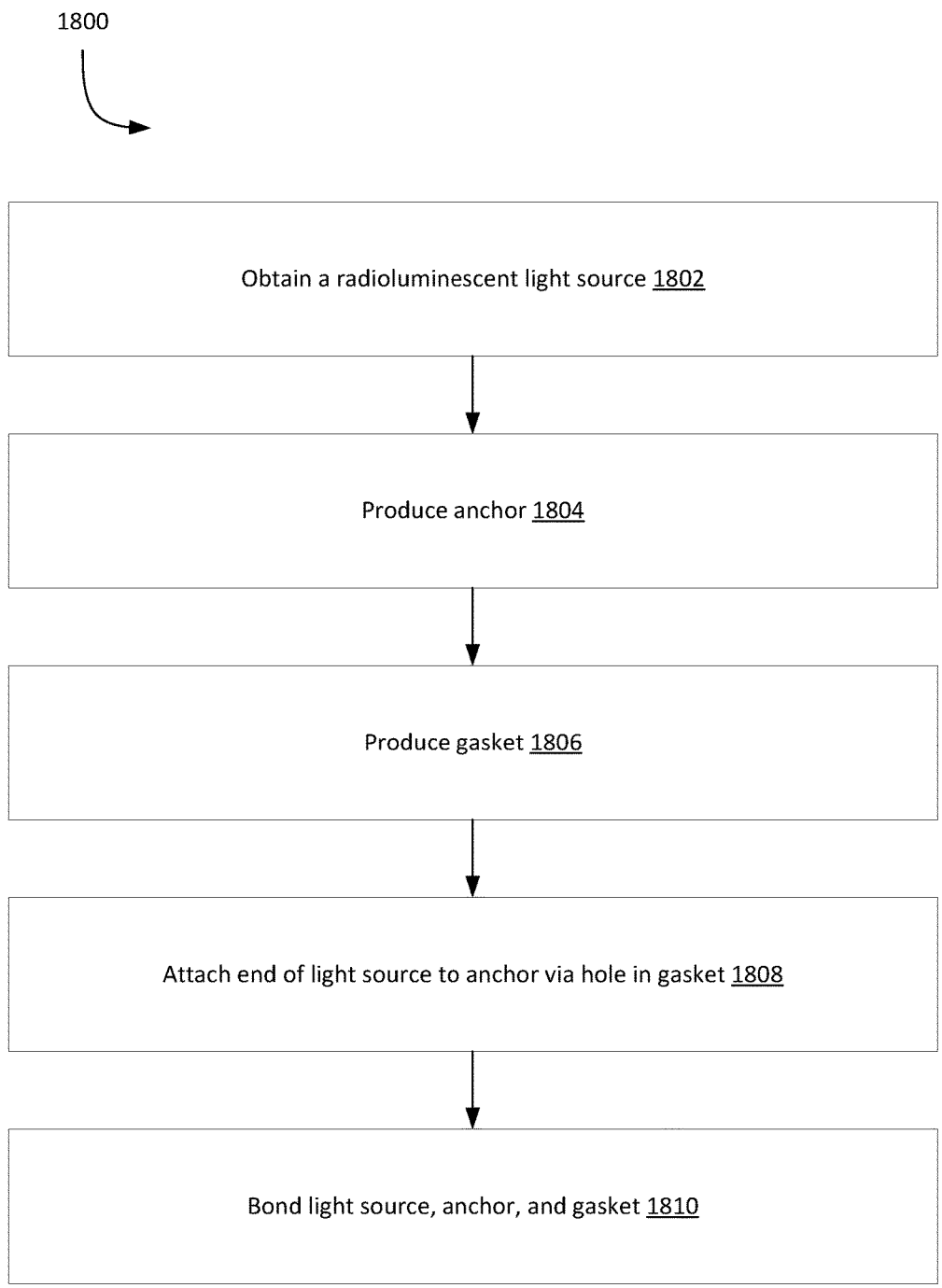
FIG. 18 is a flowchart illustrating an example of a process for manufacturing an implantable phototherapy eye device, according to embodiments of the present disclosure.

FIG. 18 is a flowchart illustrating an example of a process 1800 for manufacturing an implantable phototherapy eye device, according to embodiments of the present disclosure. The process 1800 is illustrated in connection with manufacturing an implantable phototherapy eye device that contains a light source, an anchor, and a gasket. However, steps of the process 1800 can be skipped or performed multiple times to manufacture an implantable phototherapy device that includes at least a light source and, as needed, additional light source(s), a number of anchors and/or a number of gaskets.

The process 1800 starts at step 1802 where a light source is obtained. In an example, the light source is a radioluminescent light source such as the one described in connection with FIG. 4. This light source can be obtained from a provider or can be produced directly. In an example, producing the light source includes obtaining a glass capillary that includes a first end and a second, coating an interior surface of a glass capillary with phosphor material, sealing (e.g., thermal sealing) the first end of the glass capillary, filling the glass capillary with tritium gas through the second end, and sealing (e.g., thermal sealing) the second end of the glass capillary. Once both ends are sealed, the chamber becomes hermetically sealed. In addition, an exterior surface of the glass capillary can be partially coated with a biocompatible and light-reflective material such as gold. Further, the exterior surface can be further coated with a biocompatible and light-transparent material, such as a thin layer of parylene C.

At operation 1804, an anchor for the implantable phototherapy eye device is produced. In an example, the anchor is made (e.g., includes) of a first cured polydimethylsiloxane (PDMS) material. In this example, producing the anchor includes filling grooves of a first mold with first liquid PDMS material, curing (e.g., thermal curing) the first liquid PDMS material, and removing the first cured PDMS material from the first mold.

At operation 1806, a gasket for the implantable phototherapy eye device is produced. In an example, the gasket is made (e.g., includes) of a second cured polydimethylsiloxane (PDMS) material. This PDMS material can be of the same type as the one used for the anchor. In this example, producing the gasket includes filing a partially-spherical cavity (e.g., a cavity having a hemispherical dome shape) of a second mold with second liquid PDMS material, curing (e.g., thermal curing) the second liquid PDMS material, and removing the second cured PDMS material from the second mold.

At operation 1808, an end of light source is attached to the anchor via a hole in the gasket. For example, the hole is made in the gasket by removing a portion of the second cured PDMS material, where this portion is located on top of the hemispherical dome shape of the gasket. The end of the light source is inserted in the hole and travels the height of the gasket in an uncompressed state of the gasket. This end contacts a surface of the center body of the anchor. Bonding PDMS material is applied to the center body and/or the end of the light source. Bonding PDMS material is also applied to any gap around the hole between the light source and the hole of the gasket.

At operation 1810, the light source, anchor, and gasket are bonded based on the bonding PDMS material. For example, thermal curing is applied to cure the bonding PDMS material, thereby securing the end of the light source to the anchor and sealing any gap around the hole of the gasket.

In various embodiments of the present disclosure, wearable phototherapeutic contact lenses contain one or more light sources. When worn, such contact lenses provide the treatment and prevention of ocular pathologies arising from hypoxia. Generally, a wearable contact lens can operate and be similarly effective as an implantable phototherapy eye device, without the need for surgical implantation. The configuration of the light source(s) in terms of volume, shape, and emitted light provide the desired therapeutic effect due to the light wavelength and irradiance. The underlying itself lens acts as the anchor. No gasket is needed as the wearable contact lens can be worn on the cornea of an eyeball. Unlike the implantable phototherapy eye device, one of the challenges of the wearable contact lens is sizing the light source(s) properly to support the desired therapeutic effect without blocking vision and/or flow of the oxygen into the eyeball. One approach to overcome such challenges relies on using a distributed light source. In particular, the light source is made of a number of smaller light sources (relative to the light source of the implantable phototherapy eye device). These smaller light sources are distributed across and embedded in the underlying lens. In this way, light can still enter the eyeball and oxygen can properly flow to the eyeball without being significantly blocked by the gas impermeable light sources. These and other features of the contact lens are further described in the next figures.

Figure 19:
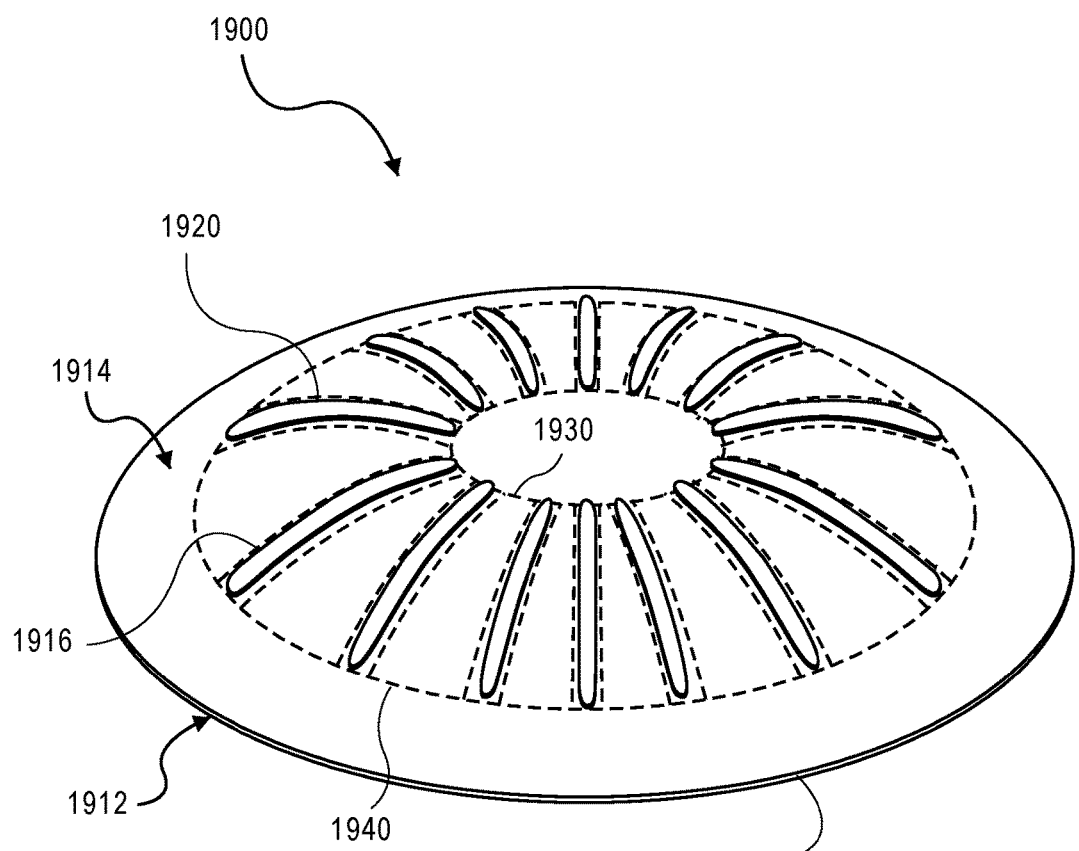
FIG. 19 illustrates an example of a wearable eye contact lens, according to embodiments of the present disclosure.

FIG. 19 illustrates an example of a wearable eye contact lens 1900, according to embodiments of the present disclosure. Generally, the contact lens 1900 includes a lens 1910 and a number of light sources 1920. The lens 1920 is flexible, biocompatible, light-transparent, and highly oxygen permeable. For example, the lens 1920 is made out of PDMS (MED-4210) material. This material allows light to enter and oxygen to flow into the eyeball. Further, each of the inside surface 1912 (e.g., interior surface relative to placement on the cornea) and, optionally, the outside surface 1914 (e.g., exterior surface relative to placement on the cornea) of the lens 1910 has a convex shape. The convex shape of the inside surface 1912 allows anchoring or attachment of the contact lens 1900 to the outside surface of the cornea of an eyeball. In particular, the inside surface 1912 of the lens 1910 sits on top of the outside surface of the cornea.

In an example, the lens has a number of chambers 1916. In turn, each of the chambers 1916 retains a number of the light sources 1920. Although FIG. 19 illustrates that each chamber houses a single light source, other configurations are possible, where a single chamber can retain multiple light sources or multiple chambers can retain a single light source. Regardless, each of the chambers 1916 is located inside the lens 1910 (e.g., between its outside surface 1914 and its inside surface 1912). In a possible configuration, a chamber 1916 retains a light source 1920 by fully containing the light source 1920. In this way, the light source 1920 is embedded inside the lens 1900.

In an example, a light source 1920 has similar components as the light source 400 of FIG. 4, except with different dimensions such that the light source 1920 is suitable for placement in a chamber 1912 of the lens 1910. For instance, the light source 1920 is a radioluminescent light source that includes one or more walls that form a second chamber (e.g., a chamber interior to the light source 1920). The radioluminescent light source can be made out of biocompatible and transparent material. Phosphor material coats at least one of the one or more walls. Radioisotope material is in the second chamber.

In a particular illustrative example, the radioisotope material includes gaseous tritium. The radioluminescent light source has an exterior volume defined by the one or more walls. This exterior volume is in the range of $6 \times 10^{-6}$ to $6 \times 10^{-5}$ cubic inch (0.1 to 1 mm³). For instance, the radioluminescent light source has a substantially cylindrical shape formed by the one or more walls. The cylindrical shape has a height in the range of to $3.9 \times 10^{-2}$ to 0.6 inch (1 to 15 mm) and a radius in the range of to $3.9 \times 10^{-3}$ to 0.01 inch (0.1 to 0.3 mm). As an example, the height is substantially $7.9 \times 10^{-2}$ inch (2 mm) and the radius of the cylindrical shape (e.g., of its top or bottom base) is substantially $6 \times 10^{-3}$ inch (0.15 mm). The cylindrical shape need not but can be slightly bent along its lateral axis such that the cylindrical shape follows the convex curvature of the lens 1900.

Given the cylindrical shape and its dimensions, and to provide the desired irradiance, the lens 1910 includes a plurality of radioluminescent light sources 1920 that are evenly distributed according to a pattern across a portion of the lens. In an example, the pattern arranges the plurality of radioluminescent light sources 1920 in a longitude pattern having an inner circle 1930 and an outer circle 1940 that are centered around a center of the lens 1900. This pattern radially orients the longitudinal axis of each of the light sources 1920 between the inner and outer circles 1930 and 1940. The end of each cylindrical shape belongs to the inner circle 1930. The opposite end of each cylindrical shape belongs to the outer circle 1940. The number of the radioluminescent light sources 1920 is in the range of twenty to thirty. In a particular illustrative example, twenty-four light sources 1920 are used. In another example, the pattern arranges the plurality of radioluminescent light sources 1920 in an annular pattern with these light sources 1920 oriented in a radial direction.

Further, to increase the irradiance from a light source 1920, a biocompatible and light-reflective material is applied to a portion of the light source 1920. For example, the light source 1920 includes an exterior surface that is oriented toward the exterior surface 1914 of the lens 1910. The light source 1920 also includes an interior surface that is oriented toward the interior surface 1912 (which is typically a convex surface) of the lens 1910. The interior surface of the light source 1920 is not coated with the light-reflective material to allow light to be emitted towards the eyeball through this surface of the light source 1920. In comparison, a portion of the exterior surface of the light source 1920 is coated with the biocompatible light-reflective material, such as gold. In a particular illustrative example, the light source 1920 is divided equally between the exterior surface and the interior surface. The exterior surface is fully coated with gold, thereby increasing the irradiance of the light source 1920 on the retina by up to fifty percent.

Hence, and as illustrated in FIG. 19, a wearable phototherapeutic eye contact lens includes a contact lens having a first chamber and a radioluminescent light source. The radioluminescent light source includes one or more walls that form a second chamber. The radioluminescent light source is in the first chamber of the lens. Phosphor material coats at least one of the one or more walls. Radioisotope material is within the second chamber.

Although FIG. 19 illustrates that the different light sources 1920 have the same configuration and dimensions, variations between the light sources 1920 are possible. For example one of the light sources 1920 may use gaseous tritium, while another light source 1920 may use radium, while yet another light source 1920 may be partially coated (e.g., on its outside surface that is parallel to the outside surface 1914 of the lens 1910) with a biocompatible light-reflective material (e.g., gold).

In an example, the lens 1910 is orthokeratology contact lens. This type of lens is worn by patients typically at nighttime to reshape the cornea, allowing vision correction when the lens is removed in the morning for the remainder of the day.

Figure 20:
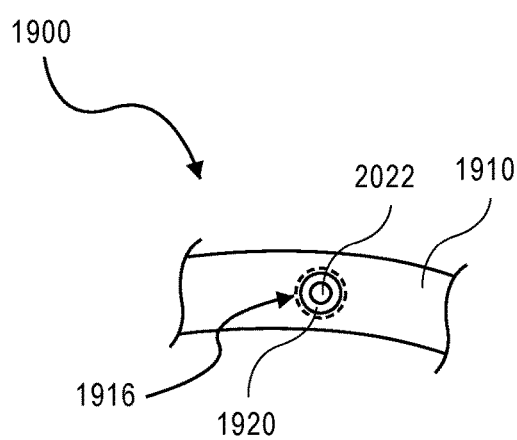
FIG. 20 illustrates a partial side view of the wearable eye contact lens of FIG. 19, according to embodiments of the present disclosure.

FIG. 20 illustrates a partial side view of the wearable eye contact lens 1900 of FIG. 19, according to embodiments of the present disclosure. As illustrated, the lens 1910 includes a chamber 1916. In turn, this chamber houses a light source 1920. In the example of a radioluminescent light source 1920, this light source 1920 includes an interior chamber 2020 having walls coated with phosphor material (e.g., zinc sulfide) and containing a radioisotope material (e.g., gaseous tritium or solid radium).

Figure 21:
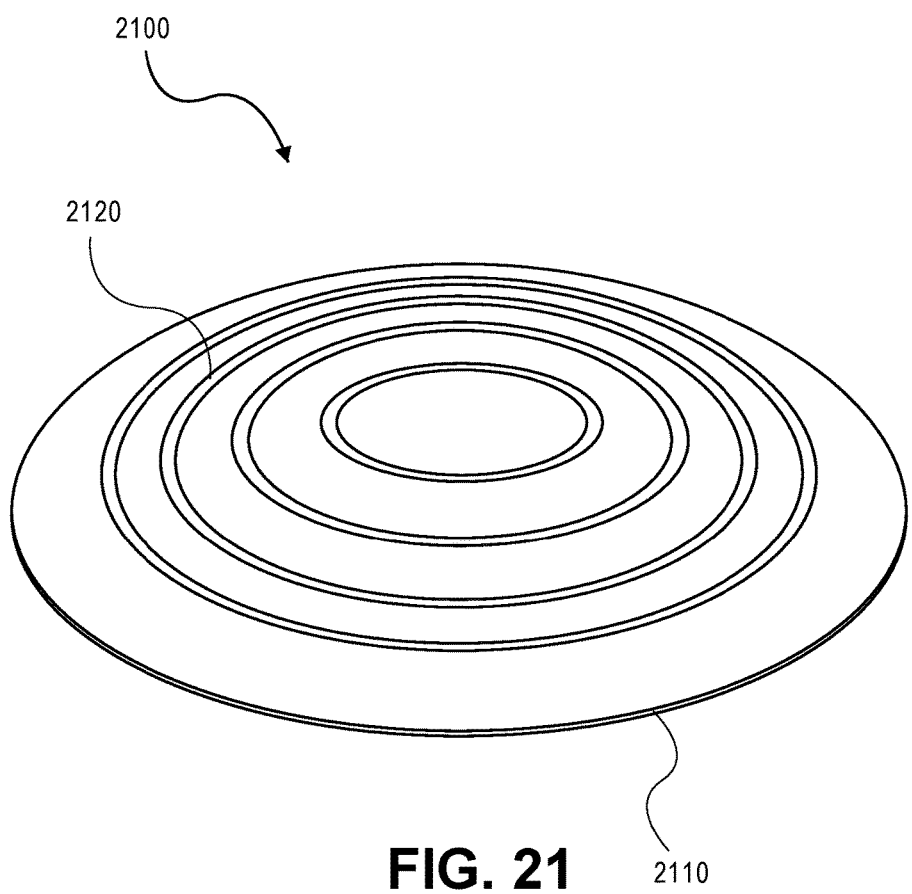
FIG. 21 illustrates another example of a wearable eye contact lens, according to embodiments of the present disclosure.

FIG. 21 illustrates another example of a wearable eye contact lens 2100, according to embodiments of the present disclosure. The components of the contact lens 2100 are similar to those of the contact lens 1900 of FIG. 19 and include a lens 2110 and a plurality of light sources 2120 embedded in the lens 2110. However, the dimensions and shapes of the light sources 2120 and their distribution pattern across the lens 2110 is different. Here, each one of the light sources 2120 has a ring shape. Alternatively, light sources with an arc shape or chord shape may approximate the ring shape. Each ring shape is a circular ring that follows the circumference of the lens 2110 and that has a different diameter than diameters of the remaining ring shapes corresponding to the remaining light sources. Accordingly, the pattern arranges the plurality of radioluminescent light sources 2020 in a ring pattern (e.g., in an annular pattern) around the center of the lens 2110. The locations of the outmost outer ring and of the inmost inner ring correspond to the outer circle 1940 and inner circle 1930 of FIG. 19, respectively.

Figure 22:
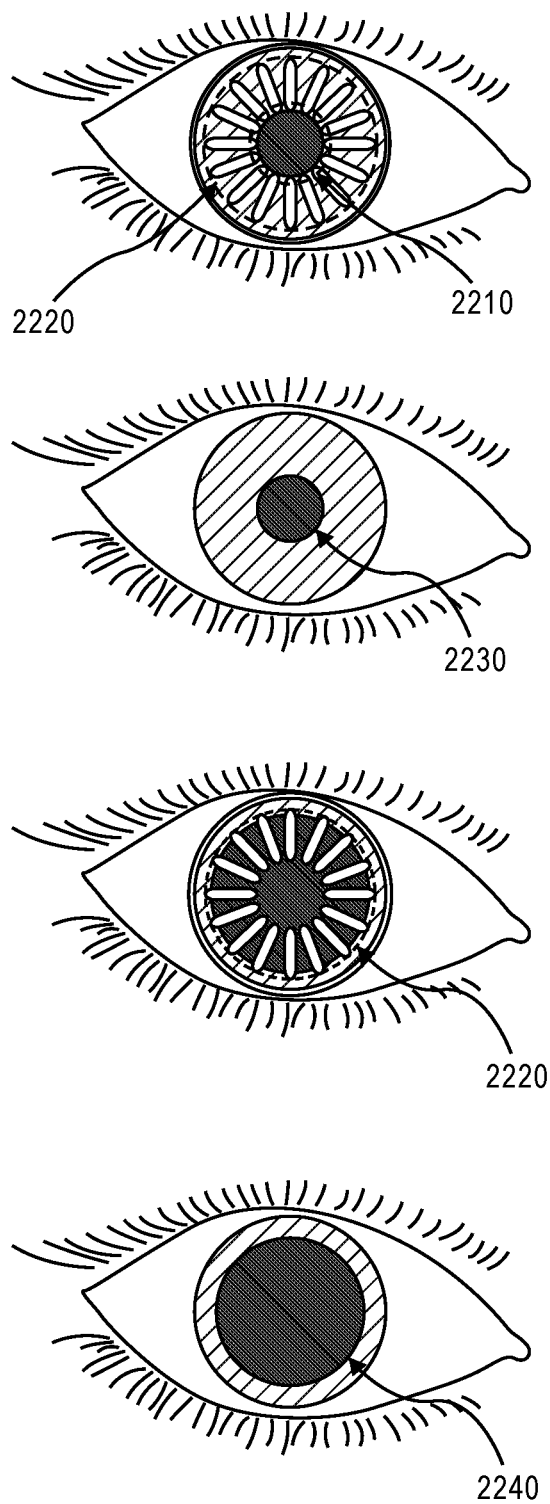
FIG. 22 illustrates placement of a wearable contact lens on an eye, according to embodiments of the present disclosure.

FIG. 22 illustrates placement of a wearable contact lens on an eye, according to embodiments of the present disclosure. In an example, the wearable contact lens has a pattern of light sources, where the pattern arranges these light sources to form an inner circle 2210 and outer circle 2220. The inner circle 2210 has a diameter that corresponds substantially to a diameter of an average human pupil in a contracted state 2230. The outer circle 2220 has a diameter that corresponds substantially to a diameter of the average human pupil in a dilated state 2240. FIG. 22 illustrates these diameters by showing that the inner circle 2210 substantially follows the perimeter of the human pupil in the contracted state 2230 and that the outer circle 2220 substantially follows the perimeter of the human pupil in the dilated state 2240.

Figure 23:
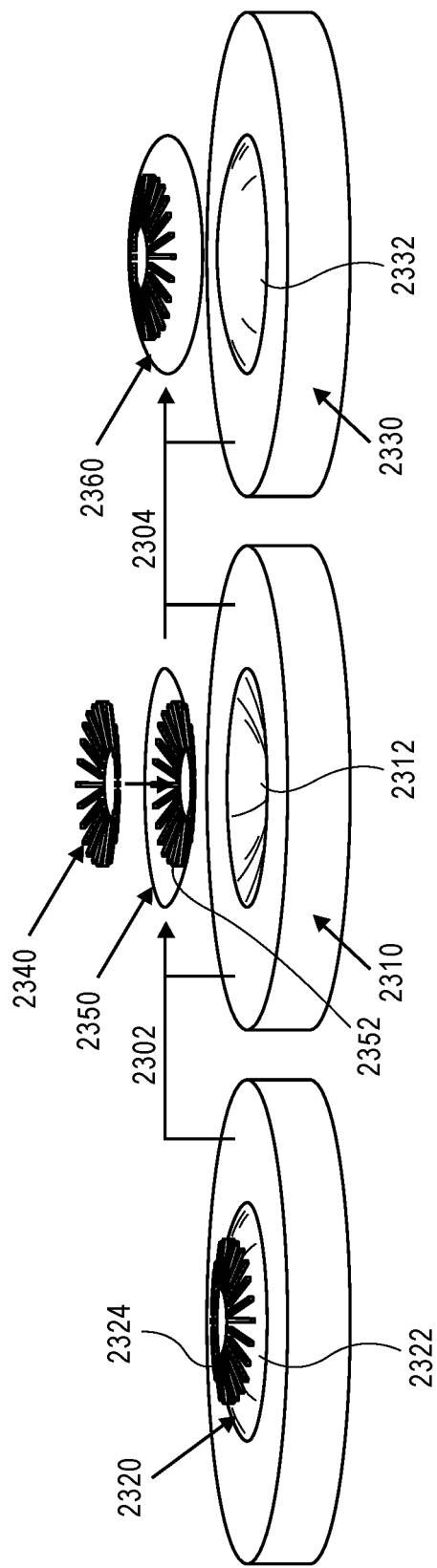
FIG. 23 illustrates an example of manufacturing a wearable contact lens, according to embodiments of the present disclosure.

FIG. 23 illustrates an example of manufacturing a wearable contact lens, according to embodiments of the present disclosure. As illustrated, the manufacturing relies on multiple molds. A first mold 2310 includes a partially spherical cavity 2312 (e.g., like a half or one third of a sphere). A second mold 2320 includes a partially spherical protrusion 2322 that can mate with the partially spherical cavity 2312 of the first mold 2310. For example, the partially spherical protrusion 2322 has a slightly smaller base diameter and height than those of the partially spherical cavity 2312. The partially spherical protrusion 2322 includes a number of indentations 2324 on its outside surface. These indentations 2324 follow a desired pattern that can be used to produce chambers in the lens and, accordingly, arrange the light sources. A third mold 2330 likewise includes partially spherical protrusion 2332 that can also mate with the partially spherical cavity 2312 of the first mold 2310. For example, the partially spherical protrusion 2332 has a slightly smaller base diameter and height than those of the partially spherical cavity 2312. However, the outer surface of this partially spherical protrusion 2332 is smooth and does not include indentations.

The manufacturing includes a first operation 2302. The operation 2302 includes filling the partially spherical cavity 2312 of the first mold 2310 with liquid PDMS (e.g. MED-4210) material and placing the second mold 2320 on the first mold 2310. In particular, the partially spherical protrusion 2322 of the second mold 2320 is placed inside the partially spherical cavity 2312 of the first mold 2310 on top of the liquid PDMS material. The operation 2302 also includes curing (e.g., thermal curing) the liquid PDMS material to form cured PDMS material 2350 having indentations 2352 corresponding to the indentations 2324 of the partially spherical protrusion 2322 of the second mold 2320. The cured PDMS material 2350 represent a portion of the lens that is being manufactured. The indentations 2352 represents walls for chambers that would contain light sources 2340. The operation 2302 also includes removing the second mold 2320 from the first mold 2310 and placing a light source 2340 (e.g., a radioluminescent light source) in each of the indentations 2352 in the cured PDMS material 2350.

In a second operation 2304 of the manufacturing, additional liquid PDMS material is placed on the cured PDMS material 2350 and the light sources 2340 placed in the indentations 2352. The operation 2304 also includes placing the third mold 2330 on the first mold 2310. In particular, the partially spherical protrusion 2332 of the third mold 2230 is placed inside the partially spherical cavity 2352 of the first mold 2310 on top of the cured PDMS material 2350, the light sources 2340, and the additional liquid PDMS material. The operation 2304 also includes curing (e.g., thermal curing) the additional liquid PDMS material (in addition to the already cured PDMS material 2350) to form a lens 2360 having chambers corresponding to the indentations 2352 of the cured PDMS material 2350. The indentations 2352 along with corresponding portions of the cured, additional PDMS material form the chambers. Each chamber includes one of the light sources 2340. The operation 2304 also includes removing the lens 2360 from the first mold 2310 and the third mold 2330.

Figure 24:
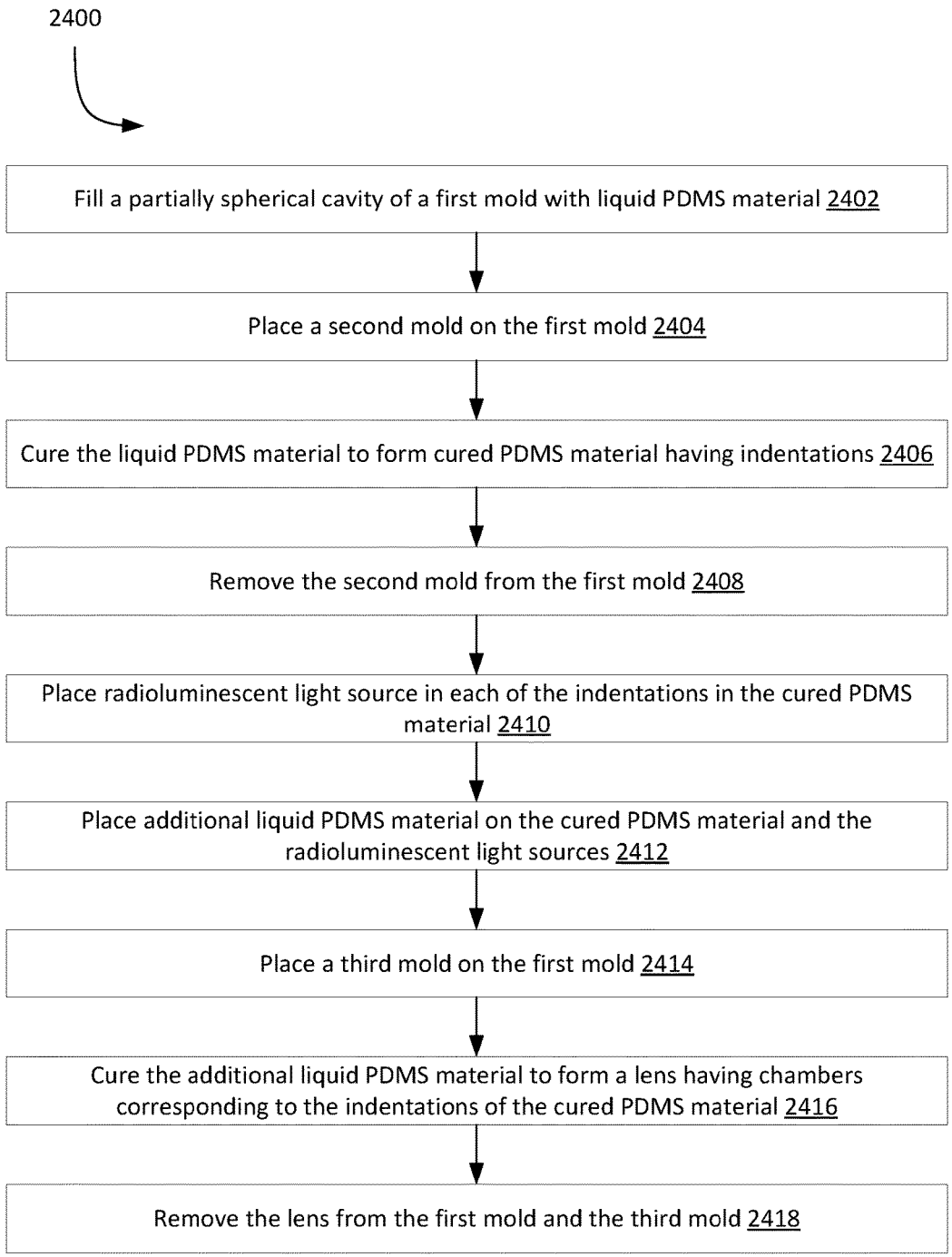
FIG. 24 is a flowchart illustrating an example of a process for manufacturing a wearable contact lens, according to embodiments of the present disclosure.

FIG. 24 is a flowchart illustrating an example of a process 2400 for manufacturing a wearable contact lens, according to embodiments of the present disclosure. The process 2400 starts at operation 2402, where a partially spherical cavity of a first mold, such as the first mold 2310 of FIG. 23, is filled with liquid PDMS material.

At operation 2404, a second mold is placed on the first mold. For example, the second mold is the second mold 2320 of FIG. 23 and includes a partially spherical protrusion having indentations. The partially spherical protrusion of the second mold is placed inside the partially spherical cavity of the first mold.

At operation 2406, the liquid PDMS material is cured to form cured PDMS material having indentations corresponding to the indentations of the partially spherical protrusion of the second mold. The cured PDMS material has a convex shape given the spherical shapes of the cavity and protrusion of the two molds.

At operation 2408, the second mold is removed from the first mold. Accordingly, a surface of the cured PDMS material becomes exposed. This surface includes the indentations and expose openings thereof.

At operation 2410, a radioluminescent light source is placed in each of the indentations in the cured PDMS material. Each of these light sources is placed through an opening in the corresponding indentation.

At operation 2412, additional liquid PDMS material is placed on the cured PDMS material and the radioluminescent light sources. For example, the additional liquid PDMS material covers the cured PDMS material, the radioluminescent light sources, any remaining openings in the indentations, and any gaps between the radioluminescent light sources and the indentations.

At operation 2414, a third mold is placed on the first mold. For example, the third mold is the third mold 2330 of FIG. 23 and includes a partially spherical protrusion having a smooth surface. The partially spherical protrusion of the third mold is placed inside the partially spherical cavity of the first mold, where the cured PDMS material, the radioluminescent light sources, and the additional liquid PDMS material are located.

At operation 2416, at least the additional liquid PDMS material is cured to form a lens having chambers corresponding to the indentations of the cured PDMS material. Each chamber includes one of the radioluminescent light sources.

At operation 2418, the lens is removed from the first mold and the third mold. This lens corresponds to a wearable eye contact lens that embeds radioluminescent light sources, similarly to the contact lens 1900 of FIG. 19.

Figure 25:
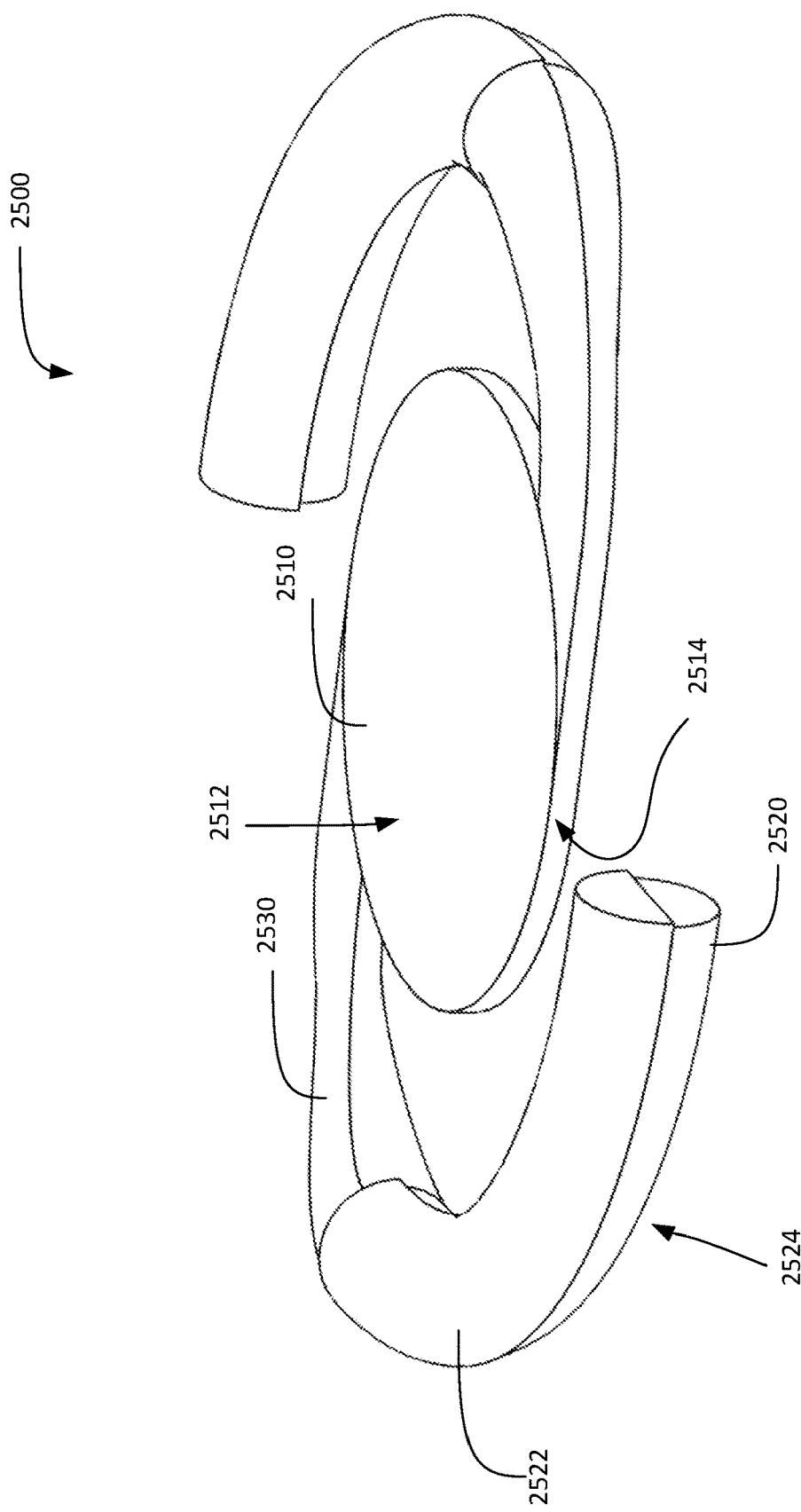
FIG. 25 illustrates an example of a phototherapy eye device implantable in a lens capsule of an eyeball, according to embodiments of the present disclosure.

FIG. 25 illustrates an example of a phototherapy eye device 2500 implantable in a lens capsule of an eyeball, according to embodiments of the present disclosure. This device 2500 is an example of an implantable phototherapy eye device suitable for intracapsular implantation (e.g., in support of the intracapsular placement 1340 of FIG. 13). The phototherapy eye device 2500 includes an arrangement of some or all of the components of the implantable device 100 of FIG. 1, where these components may be coupled with an intraocular lens 2510. The intraocular lens 2510 is typically referred to in the industry as "intraocular lenses," "implantable contact lenses," or simply "IOL."

In an example, the phototherapy eye device 2500 includes a number of biocompatible radioluminescent light sources 2520 and a number of anchors 2530. An anchor 2530 attaches a biocompatible radioluminescent light source 2520 to the intraocular lens 2510. As illustrated in FIG. 25, two biocompatible radioluminescent light sources 2520 are used, each of which is connected to the intraocular lens 2510 with one anchor 2530. However, the embodiments of the phototherapy eye device 2500 are not limited as such. Instead, a different number of biocompatible radioluminescent light sources 2520 can be used (e.g., one, three, etc.). Further, a different number of anchors 230 can be used (e.g., two per radioluminescent light source 2520). Likewise, an anchor may 230 not be attached to the intraocular lens 2510. Instead, this anchor 230 may attach two or more biocompatible radioluminescent light sources 2520, one of which may be attached to the intraocular lens 2510 directly or via another anchor 2530. In addition, no anchor 2530 may be used. For instance, the phototherapy eye device 2500 includes a number of biocompatible radioluminescent light sources 2520, each of which are directly connected to the intraocular lens 2510 or to each other (e.g., in a chain arrangement). This can be case of a monobloc-plate style intraocular lens, where a biocompatible radioluminescent light source 2520 can be incorporated into the plate portion of the lens.

Generally, a biocompatible radioluminescent light source 2520 and an anchor 2530 (if one is used) are placed externally to the intraocular lens 2510 at a position and orientation that does not impact the transparency (or flow of light) through the intraocular lens 2510. For example, and as illustrated in FIG. 25, the intraocular lens has substantially a disc like shape. Light enters primarily from a top surface 2512 of this disc and exists from the opposite, bottom surface (not illustrated) towards the retina (when the biocompatible radioluminescent light source 2520 is implanted in the eyeball). In this example, each of the anchor 2530 is connected at one end to a side (or a side surface 2514) of the disc, where this side does not serve as the primary input of light to the intraocular lens 2510. The opposite end of each anchor (or some other end) is connected to one of the two biocompatible radioluminescent light sources 2520. In this way, the biocompatible radioluminescent light sources 2520 and the anchors 2530 do not occlude the top surface 2512, thereby, do not significantly impact the flow of light through the intraocular lens 2510.

As illustrated in FIG. 25, each anchor 2530 has substantially an annular chamfered shape. For instance, the anchor 2530 is a strut, an arm, or a wing that is annular along its body. The body transitions from found to flat along the annular orientation. One end of an anchor 2530 is circular and connects to a circular base of a biocompatible radioluminescent light source 2520. Another end of the anchor 2530 is rectangular across a vertical plane and connects to the intraocular lens 2510. These connections are bonding, where PDMS (e.g., (MED-4210) is used to bond each end to the biocompatible radioluminescent light source 2520 or intraocular lens 2510. The anchor 2530 can also be made out of PDMS material. The anchors 2530 and the biocompatible radioluminescent light sources 2520 act as haptics to hold the intraocular lens 2510 in place within the lens capsule of the eyeball (once the phototherapy eye device 2500 is implanted in the lens capsule).

Each of the biocompatible radioluminescent light sources 2520 is substantially cylindrical in shape. In the case where the intraocular lens 2510 has a circular side 2514, the lateral wall of the cylinder can be bent to provide an annular orientation of the biocompatible radioluminescent light source 2520, such that the lateral wall of its cylinder is parallel to the circular side 2514 of the intraocular lens 2510. Of course, other possible shapes and arrangements of the anchors 2530 and biocompatible radioluminescent light sources 2520 are possible including arrangements to form hook and arc-like shapes.

In an example, a biocompatible and light-reflective material 2522 is applied to a portion of a biocompatible radioluminescent light source 2520 to increase the light emission from this light source 2520 in a particular direction. As illustrated in FIG. 25, the biocompatible radioluminescent light source 2520 is divided between top and bottom surfaces (bottom surface indicated with element number 2524 in the figure) along its center axis. The top surface corresponds to the top surface 2512 of intraocular lens 2510 through which light enters. The bottom surface 524 corresponds to the bottom surface of intraocular lens 2510 through which light exits. Gold 2522 (or some other biocompatible and light-reflective material) is coated on the top surface. Emitted light from the biocompatible radioluminescent light source 2520 exits from the bottom surface 2524. Hence, the top surface coating can increase the irradiance of the emitted light by up to fifty percent.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. "About" and "substantially" in reference to a diameter, radius, height, volume, or irradiance, wavelength, or other engineering units include measurements or settings that are within ±1%, ±2%, ±5%, ±10%, or other tolerances of the specified engineering units as known in the art.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. An element proceeded by "a" or "an" does not, without further constraints, preclude the existence of additional identical elements in the process, method, article, or apparatus that comprises the element.

The abstract of the disclosure is provided to allow the reader to quickly ascertain the nature of the technical disclosure. It is submitted with the understanding that it will not be used to interpret or limit the scope or meaning of the claims. In addition, in the foregoing detailed description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the detailed description, with each claim standing on its own as a separately claimed subject matter.

What is claimed is:

1. A wearable phototherapeutic eye device comprising:
   a lens having a transparent portion;
   a set of chambers positioned in the wearable phototherapeutic device relative to a circle that surrounds the transparent portion of the lens, each of the chambers surrounding annularly the circle or extending radially from the circle, the set of chambers being outside of the transparent portion and comprising a first chamber; and
   a radioluminescent light source comprising one or more walls that form a second chamber, wherein:
      the radioluminescent light source is in the first chamber of the lens,
      phosphor material coats at least one of the one or more walls, and
      radioisotope material is within the second chamber.

2. The wearable phototherapeutic eye device of claim 1, wherein the radioisotope material comprises gaseous tritium.

3. The wearable phototherapeutic eye device of claim 2, wherein the radioluminescent light source has an exterior volume defined by the one or more walls, and wherein the exterior volume is in the range of 0.1 $mm^3$ to 1 $mm^3$.

4. The wearable phototherapeutic eye device of claim 3, wherein the radioluminescent light source has a cylindrical shape formed by the one or more walls, and wherein the cylindrical shape has a height in the range of 1 mm to 15 mm.

5. The wearable phototherapeutic eye device of claim 4, wherein the height is substantially 2 mm, and wherein a radius of the cylindrical shape is substantially 0.15 mm.

6. The wearable phototherapeutic eye device of claim 1, wherein the lens comprises a plurality of radioluminescent light sources that are evenly distributed according to a pattern across a portion of the lens, wherein each one of the plurality of radioluminescent light sources has a cylindrical shape, wherein the pattern arranges the plurality of radioluminescent light sources in a longitude pattern having an inner circle and an outer circle that are centered around a center of the lens, wherein an end of each cylindrical shape belongs to the inner circle, and wherein an opposite end of each cylindrical shape belongs to the outer circle.

7. The wearable phototherapeutic eye device of claim 6, wherein the inner circle has a diameter that corresponds substantially to a diameter of an average human pupil in a contracted state, and wherein the outer circle has a diameter that corresponds substantially to a diameter of the average human pupil in a dilated state, wherein a total number of the plurality of the radioluminescent light sources is in the range of twenty to thirty radioluminescent light sources.

8. The wearable phototherapeutic eye contact lens of claim 6, wherein a total number of the plurality of the radioluminescent light sources is in the range of twenty to thirty radioluminescent light sources.

9. The wearable phototherapeutic eye contact lens of claim 1, wherein the lens comprises a plurality of radioluminescent light sources that are evenly distributed according to a pattern across a portion of the lens.

10. The wearable phototherapeutic eye contact lens of claim 9, wherein each one of the plurality of radioluminescent light sources has a ring shape that has a different diameter than diameters of the remaining radioluminescent light sources, wherein the pattern arranges the plurality of radioluminescent light sources in a ring pattern around a center of the lens.

11. The wearable phototherapeutic eye contact lens of claim 1, wherein the lens has an interior convex surface and an exterior surface, wherein a portion of an exterior surface of the radioluminescent light source is coated with a biocompatible reflective material, wherein a remaining portion of the exterior surface of the radioluminescent light source is uncoated with the biocompatible reflective material and is oriented toward the interior convex surface of the lens, and wherein the portion of the exterior surface of the radioluminescent light source coated with the biocompatible reflective material is oriented toward the exterior surface of the lens.

12. The wearable phototherapeutic eye contact lens of claim 1, wherein the lens is an orthokeratology contact lens.

* * * * *